United States Patent
Kobayashi

(10) Patent No.: US 9,492,568 B2
(45) Date of Patent: Nov. 15, 2016

(54) METHOD FOR SUPPRESSING CELL GROWTH

(75) Inventor: Hideki Kobayashi, Yokosuka (JP)

(73) Assignee: JAPAN AGENCY FOR MARINE-EARTH SCIENCE AND TECHNOLOGY, Kanagawa (JP)

( * ) Notice: Subject to any disclaimer, the term of this patent is extended or adjusted under 35 U.S.C. 154(b) by 1173 days.

(21) Appl. No.: 13/132,911

(22) PCT Filed: Dec. 2, 2009

(86) PCT No.: PCT/JP2009/006551
§ 371 (c)(1),
(2), (4) Date: Aug. 19, 2011

(87) PCT Pub. No.: WO2010/064425
PCT Pub. Date: Jun. 10, 2010

(65) Prior Publication Data
US 2011/0300631 A1    Dec. 8, 2011

(30) Foreign Application Priority Data

Dec. 5, 2008 (JP) ................................. 2008-311106

(51) Int. Cl.
| | |
|---|---|
| C12P 21/06 | (2006.01) |
| A61K 48/00 | (2006.01) |
| C12N 15/67 | (2006.01) |
| C12N 7/00 | (2006.01) |

(52) U.S. Cl.
CPC ............ *A61K 48/005* (2013.01); *C12N 15/67* (2013.01); *C12N 2830/002* (2013.01)

(58) Field of Classification Search
CPC ................ A61K 48/005; C12N 15/67; C12N 2830/002
See application file for complete search history.

(56) References Cited

U.S. PATENT DOCUMENTS

2005/0196865 A1 * 9/2005 Frazer ........................... 435/456
2006/0292566 A1   12/2006 Frazer

FOREIGN PATENT DOCUMENTS

| EP | 1 591 523 A1 | 2/2005 | |
|---|---|---|---|
| WO | WO 99/02694 | 1/1999 | |
| WO | WO 2004/050878 | * 6/2004 | ............. C12N 15/67 |

OTHER PUBLICATIONS

Japanese Office Action for corresponding JP Application No. 2008-311106, Jul. 16, 2013.

(Continued)

*Primary Examiner* — Reza Ghafoorian
(74) *Attorney, Agent, or Firm* — Ditthavong & Steiner, P.C.

(57) ABSTRACT

Disclosed is a method for suppressing the growth of a target cell, which is not limited in the type of a target cell and the type of a protein to be expressed in the target cell and needs not any preparatory experiment for determining a codon to be contained in a protein to be expressed in a target cell. Specifically disclosed is a method for suppressing the growth of a target cell, which comprises the steps of: incorporating DNA containing a region encoding a protein into the target cell, and allowing a protein encoded by the DNA to be expressed in the target cell into which the DNA has been incorporated. The region contained in the DNA comprises a tri-nucleotide sequence. The tri-nucleotide sequence is selected from codons that define at least some amino acid species constituting the protein, and is complementary to at least some codons that are used in the target cell at a frequency of 0.2 or less.

9 Claims, 10 Drawing Sheets

(56) References Cited

OTHER PUBLICATIONS

Molecular Cloning: A laboratory manual, 2$^{nd}$ Edition, Cold Spring Harbor Laboratory. Cold Spring Harbor, NY, 1989.
Current Protocols in Molecular Biology, Supplement 1~38, John Wiley & Sons (1987-1997) Disclosed at http://onlinelibrary.wiley.com/book/10.1002/0471142727/homepage/archive.htm.
Extended European Search Report for corresponding EP Application No. 09830195.5-1410, Apr. 22, 2013.
K Zahn, "Overexpression of an mRNA dependent on rare codons inhibits protein synthesis and cell growth.", Journal of Bacteriology, May 1, 1996, p. 2926-2933, vol. 178, No. 10.
J. J. Olivares-Trejo et al., "The pair of arginine codons AGA AGG close to the initiation codon of the lambda int gene inhibits cell growth and protein synthesis by accumulating peptidyl-tRNAArg4", Molecular Microbiology, Aug. 1, 2003, p. 1043-1049, vol. 49, No. 4, Blackwell Publishing Ltd.
K V Konan et al., "Importance of the Two Interferon-stimulated Response Element(ISRE) Sequences in the Regulation of the Human Indoleamine 2,3-Dioxygenase Gene.", The Journal of Biological Chemistry, Aug. 1, 1996, p. 19140-19145, vol. 271, No. 32.
J. Beekwilder et al., "A phagemid vector using the *E. coli* phage shock promoter facilitates phage display of toxic proteins", Gene, Mar. 4, 1999, p. 23-31, vol. 228, No. 1-2.
Grzegorz Kudla et al., "Coding-Sequence Determinants of Gene Expression in *Escherichia coli*", Science, Apr. 10, 2009, p. 255-258, vol. 324, No. 5924.
Fumiaki, Y., Yoshiki, A., Akira, M., Toshimichi, I. & Syozo, O., Nucleic Acids Res. 19, 6119-6122 (1991).
Makrides, S. C., Microbiol Rev. 60, 512-538 (1996).
Sharp, P. M. & Matassi, Curr Opin Genet Dev. 4, 851-860 (1994).
Bulmer, M. Genetics, 149, 897-907 (1991).
Sharp, P. M., Stenico, M., Peden, J. F. &Lloyd, A. T. Biochem. Soc. Trans. 21,835-841 (1993).
Ikemura, T.,J. Mol.Biol. 151, 389-409 (1981).
Ikemura, T.,Mol. Biol. Evol. 2, 13-34 (1985).
Sharp, P. M. & Li, W., J. Mol. Evol. 24, 28-38(1986).
Anderson, S. G. E.. & Kurland, C. G., Microbiol.Rev. 54, 198-210 (1990).
J. Am. Chem. Soc., 89, 4801 (1967).
J. Am. Chem. Soc., 91, 3350 (1969).
Science, 150, 178 (1968).
Tetrahedron Lett., 22. 1859 (1981).
Tetrahedron Lett., 24. 245 (1983).
Methods in Enzymology, 154, 350, 367-382 (1987).
Methods in Enzymology, 100, 468 (1983).
Nucleic Acids Res., 12, 9441 (1984).
Course 1, Cont'd Biochemistry Experiments, "Genetic Research Methods II," comp. by the Japanese Biochemical Society, p. 105 (1986).
Paun A, Pitha PM, Biochimie. 2007 89(6-7):744-53.
Ozato K, Tailor P, Kubota T., J Biol Chem. 2007 282(28) :20065-9.
Hiscott J. Pitha P. Genin P. Nguyen H. Heylbroeck C. Mamane Y, Algarte M, Lin R., J Interferon Cytokine Res. 1999 19(1):1-13.
Nakamura, y., Gojobori, T. & Ikemura, T., (2000), Nucleic Acids Res. 28. 292.
Kobayashi, H. et al., (2004), Proc. Natl Acad. Sci. USA 101, 8414-8419.
Sikorski, R. S. & Herter, P., (1989), Genetics 122, 19-27.
Coleman, J. E ., (1992) . Annu Rev. Biophys. Chem. 21, 441-483.
Cormack, B. P., Valdivia. R. H. & Falkow, S., (1996), Gene173. 33-38.
Carbone, A., Zinovyev, A & Kepes, F., (2003) Bioinformatics, 19, 2005-2015.
Gardner, T. S., Cantor, C. R. & Collins, J. J., (2000), Nature 403, 339-342.
Wilson, I. B., Dayan, J. & Cyr, K., (1964), J. Biol. Chem. 239, 4182-4185.
Magnusson, L. U., Farewell, A. & Nystrom, T., (2005), Trends Microbiol. 13, 236-242.
Cormack, B. P. et al., (1997), Microbiology 143, 303-311.
Auxilien, S., Crain, P. F., Trewyn, R. W. & Grosjean, H. H., (1996), J. Mol. Biol. 262, 437-458.
Lodish, H. F. et al., (2004), Molecular Cell Biology, W H Freeman & Co., New York.
Blake, W. J., Kaern, M., Cantor, C. R. & Collins, J. J., (2003), Nature 422, 633-637.
Kellis, M., Birren, B. W. & Lander, E. C., (2004), Nature 428, 617-624.
Soma, A. et al., (2003), Mol. Cell 12, 689-698.
Birge, E. A., (2000), Bacterial and Bacteriophage Genetics, Springer-Verlag. New York, ed. 4.
International Preliminary Report on Patentability (Chapter I) with Translation of Written Opinion of the International Searching Authority (w/International Preliminary Report) for corresponding International Application No. PCT/JP2009/006551, Jul. 5, 2011.
International Search Report for corresponding International Application No. PCT/JP2009/006551, Dec. 28, 2009.
Office Action for corresponding European Application No. 09 830 195.5, dated Apr. 15, 2014, 9 pages.
Mueller et al., "Reduction of the Rate of Poliovirus Protein Synthesis Through Large-Scale Condon Deoptimization Causes Attenuation of Viral Virulence by Lowering Specific Infectivity", Journal of Virology, Oct. 2006, vol. 80, No. 19, pp. 9687-9696.
Westwood et al., "Improved Recombinant Protein Yield Using a Condon Deoptimized DHFR Selectable Marker in a CHEF1 Expression Plasmid", Biotechnol. Prog., 2010, vol. 26, No. 6, pp. 1558-1566.

* cited by examiner

SEQUENCE LISTING

```
<160> NUMBER OF SEQ ID NOS: 11

<210> SEQ ID NO 1
<211> LENGTH: 717
<212> TYPE: DNA
<213> ORGANISM: Artificial sequence
<220> FEATURE:
<223> OTHER INFORMATION: mutated GFP gene

<400> SEQUENCE: 1
atgtcaaagg gggaggagct attcacaggg gtagtaccca tactagtaga gctagacggg      60
gacgtaaatg ggcaaaagtt ctcagtatca ggggagggggg aggggggacgc tacatacggg     120 aagctaacac taaagttcat atgtacaaca gggaagctac ccgtaccctg gcccacacta     180
```

```
gtaacaacat tcgggtacgg ggtacaatgt ttcgctaggt accccgacca catgaagcaa      240
cacgacttct tcaagtcagc tatgcccgag gggtacgtac aagagaggac aatattctac      300
aaggacgacg ggaattacaa gacaagggct gaggtaaagt tcgaggggga cacactagta      360
aataggatag agctaaaggg gatagacttc aaggaggacg ggaatatact agggcacaag      420
atggagtaca attacaattc acacaatgta tacataatgg ctgacaagcc caagaatggg      480
ataaaggtaa atttcaagat aaggcacaat ataaggacg ggtcagtaca actagctgac       540
cactaccaac aaaatacacc catagggac gggcccgtac tactcccga caatcactac        600 ctatcaacac aatcagctct atcaaaggac cccaatgaga agaggacca catgatacta       660 ctagagttcg taacagctgc tgggataaca cacgggatgg acgagctata caagtag        717

<210> SEQ ID NO 2
<211> LENGTH: 537
<212> TYPE: DNA
<213> ORGANISM: Artificial sequence
<220> FEATURE:
<223> OTHER INFORMATION: mutated GFP gene (75%)

<400> SEQUENCE: 2
atgtcaaagg gggaggagct attcacaggg gtagtaccca tactagtaga gctagacggg       60
gacgtaaatg ggcaaaagtt ctcagtatca ggggaggggg aggggacgc tacatacggg      120 aagctaacac taaagttcat atgtacaaca gggaagctac ccgtaccctg gcccacacta      180
gtaacaacat tcgggtacgg ggtacaatgt ttcgctaggt accccgacca catgaagcaa      240
cacgacttct tcaagtcagc tatgcccgag gggtacgtac aagagaggac aatattctac      300
aaggacgacg ggaattacaa gacaagggct gaggtaaagt tcgaggggga cacactagta      360
aataggatag agctaaaggg gatagacttc aaggaggacg ggaatatact agggcacaag      420
atggagtaca attacaattc acacaatgta tacataatgg ctgacaagcc caagaatggg      480
ataaaggtaa atttcaagat aaggcacaat ataaggacg ggtcagtaca actatag         537

<210> SEQ ID NO 3
<211> LENGTH: 360
<212> TYPE: DNA
<213> ORGANISM: Artificial sequence
<220> FEATURE:
<223> OTHER INFORMATION: Mutated GFP gene (50%)

<400> SEQUENCE: 3
atgtcaaagg gggaggagct attcacaggg gtagtaccca tactagtaga gctagacggg       60
gacgtaaatg ggcaaaagtt ctcagtatca ggggaggggg aggggacgc tacatacggg      120 aagctaacac taaagttcat atgtacaaca gggaagctac ccgtaccctg gcccacacta      180
gtaacaacat tcgggtacgg ggtacaatgt ttcgctaggt accccgacca catgaagcaa      240
cacgacttct tcaagtcagc tatgcccgag gggtacgtac aagagaggac aatattctac      300
aaggacgacg ggaattacaa gacaagggct gaggtaaagt tcgaggggga cacactatag     360

<210> SEQ ID NO 4
<211> LENGTH: 180
<212> TYPE: DNA
<213> ORGANISM: Artificial sequence
<220> FEATURE:
<223> OTHER INFORMATION: Mutated GFP gene (25%)

<400> SEQUENCE: 4
atgtcaaagg gggaggagct attcacaggg gtagtaccca tactagtaga gctagacggg       60
```

```
gacgtaaatg ggcaaaagtt ctcagtatca ggggagggg aggggacgc tacatacggg      120 aagctaacac taaagttcat atgtacaaca gggaagctac ccgtaccctg gcccacatag    180
```

<210> SEQ ID NO 5
<211> LENGTH: 717
<212> TYPE: DNA
<213> ORGANISM: Artificial sequence
<220> FEATURE:
<223> OTHER INFORMATION: Mutated GFP gene

<400> SEQUENCE: 5

```
atgagcaaag gcgaagaact gtttaccggc gtggtgccga ttctggtgga actggatggc     60
gatgtgaacg gccagaaatt tagcgtgagc ggcgaaggcg aaggcgatgc gacctatggc    120
aaactgaccc tgaaatttat ttgcaccacc ggcaaactgc cggtgccgtg gccgaccctg    180
gtgaccacct ttggctatgg cgtgcagtgc tttgcgcgct atccggatca tatgaaacag    240
catgattttt ttaaaagcgc gatgccggaa ggctatgtgc aggaacgcac cattttttat    300
aaagatgatg gcaactataa aacccgcgcg gaagtgaaat ttgaaggcga taccctggtg    360
aaccgcattg aactgaaagg cattgatttt aaagaagatg gcaacattct gggccataaa    420
atggaatata actataacag ccataacgtg tatattatgg cggataaacc gaaaaacggc    480
attaaagtga actttaaaat tcgccataac attaaagatg gcagcgtgca gctggcggat    540
cattatcagc agaacacccc gattggcgat ggcccggtgc tgctgccgga taaccattat    600
ctgagcaccc agagcgcgct gagcaaagat ccgaacgaaa aacgcgatca tatgattctg    660
ctggaatttg tgaccgcggc gggcattacc catggcatgg atgaactgta taaataa      717
```

<210> SEQ ID NO 6
<211> LENGTH: 537
<212> TYPE: DNA
<213> ORGANISM: Artificial sequence
<220> FEATURE:
<223> OTHER INFORMATION: Mutated GFP gene (75%)

<400> SEQUENCE: 6

```
atgagcaaag gcgaagaact gtttaccggc gtggtgccga ttctggtgga actggatggc     60
gatgtgaacg gccagaaatt tagcgtgagc ggcgaaggcg aaggcgatgc gacctatggc    120
aaactgaccc tgaaatttat ttgcaccacc ggcaaactgc cggtgccgtg gccgaccctg    180
gtgaccacct ttggctatgg cgtgcagtgc tttgcgcgct atccggatca tatgaaacag    240
catgattttt ttaaaagcgc gatgccggaa ggctatgtgc aggaacgcac cattttttat    300
aaagatgatg gcaactataa aacccgcgcg gaagtgaaat ttgaaggcga taccctggtg    360
aaccgcattg aactgaaagg cattgatttt aaagaagatg gcaacattct gggccataaa    420
atggaatata actataacag ccataacgtg tatattatgg cggataaacc gaaaaacggc    480
attaaagtga actttaaaat tcgccataac attaaagatg gcagcgtgca gctgtaa       537
```

<210> SEQ ID NO 7
<211> LENGTH: 1128
<212> TYPE: DNA
<213> ORGANISM: Artificial sequence
<220> FEATURE:
<223> OTHER INFORMATION: Mutated b-actin

<400> SEQUENCE: 7

```
atggatgatg atatagcggc gctagtagta gataatggtt cgggtatgtg taaagcgggt     60
```

```
tttgcgggtg atgatgcgcc gcgtgcggta tttccgtcga tagtaggtcg tccgcgtcat    120
caaggtgtaa tggtaggtat gggtcaaaaa gattcgtatg taggtgatga agcgcaatcg    180
aaacgtggta tactaacgct aaaatatccg atagaacatg gtatagtaac gaattgggat    240
gatatggaaa aaatatggca tcatacgttt tataatgaac tacgtgtagc gccggaagaa    300
catccggtac tactaacgga agcgccgcta atccgaaag cgaatcgtga aaaaatgacg     360
caaataatgt ttgaaacgtt taatacgccg gcgatgtatg tagcgataca agcggtacta    420
tcgctatatg cgtcgggtcg tacgacgggt atagtaatgg attcgggtga tggtgtaacg    480
catacggtac cgatatatga aggttatgcg ctaccgcatg cgatactacg tctagatcta    540
gcgggtcgtg atctaacgga ttatctaatg aaaatactaa cggaacgtgg ttattcgttt    600
acgacgacgg cggaacgtga atagtacgt gatataaaag aaaaactatg ttatgtagcg     660
ctagattttg aacaagaaat ggcgacggcg gcgtcgtcgt cgtcgctaga aaaatcgtat    720
gaactaccgg atggtcaagt aataacgata ggtaatgaac gttttcgttg tccggaagcg    780
ctatttcaac cgtcgtttct aggtatggaa tcgtgtggta tacatgaaac gacgtttaat    840
tcgataatga aatgtgatgt agatatacgt aaagatctat atgcgaatac ggtactatcg    900
ggtggtacga cgatgtatcc gggtatagcg gatcgtatgc aaaaagaaat aacggcgcta    960
gcgccgtcga cgatgaaaat aaaaataata gcgccgccgg aacgtaaata ttcggtatgg   1020
ataggtggtt cgtactagc gtcgctatcg acgtttcaac aaatgtggat atcgaaacaa    1080
gaatatgatg aatcgggtcc gtcgatagta catcgtaaat gtttttag                1128
```

<210> SEQ ID NO 8
<211> LENGTH: 1008
<212> TYPE: DNA
<213> ORGANISM: Artificial sequence
<220> FEATURE:
<223> OTHER INFORMATION: Mutated GAPDH gene
<400> SEQUENCE: 8

```
atgggtaaag taaaagtagg tgtaaatggt tttggtcgta taggtcgtct agtaacgcgt     60
gcggcgttta attcgggtaa agtagatata gtagcgataa atgatccgtt tatagatcta    120
aattatatgg tatatatgtt tcaatatgat tcgacgcatg gtaaatttca tggtacggta    180
aaagcggaaa atggtaaact agtaataaat ggtaatccga taacgatatt tcaagaacgt    240
gatccgtcga aaataaaatg gggtgatgcg ggtgcggaat atgtagtaga atcgacgggt    300
gtatttacga cgatggaaaa agcgggtgcg catctacaag gtggtgcgaa acgtgtaata    360
atatcggcgc cgtcggcgga tgcgccgatg tttgtaatgg gtgtaaatca tgaaaaatat    420
gataattcgc taaaaataat atcgaatgcg tcgtgtacga cgaattgtct agcgccgcta    480
gcgaaagtaa tacatgataa ttttggtata gtagaaggtc taatgacgac ggtacatgcg    540
ataacggcga cgcaaaaaac ggtagatggt ccgtcgggta aactatgcg tgatggtcgt     600 ggtgcgctac aaaatataat accggcgtcg acgggtgcgg cgaaagcggt aggtaaagta    660
ataccggaac taaatggtaa actaacgggt atggcgtttc gtgtaccgac ggcgaatgta    720
tcggtagtag atctaacgtg tcgtctagaa aaaccggcga aatatgatga tataaaaaaa    780
gtagtaaaac aagcgtcgga aggtccgcta aaaggtatac taggttatac ggaacatcaa    840
gtagtatcgt cggatttaaa ttcggatacg cattcgtcga cgtttgatgc gggtgcgggt    900
atagcgctaa atgatcattt tgtaaaaacta atatcgtggt atgataatga atttggttat    960
tcgaatcgtg tagtagatct aatggcgcat atggcgtcga aagaatag                 1008
```

<210> SEQ ID NO 9
<211> LENGTH: 1584
<212> TYPE: DNA
<213> ORGANISM: Artificial sequence
<220> FEATURE:
<223> OTHER INFORMATION: Mutated tyrosine kinase

<400> SEQUENCE: 9

| | |
|---|---|
| atgatactat cgtcgtataa tacgatacaa tcggtatttt gttgttgttg ttgttgttcg | 60 |
| gtacaaaaac gtcaaatgcg tacgcaaata tcgctatcga cggatgaaga actaccggaa | 120 |
| aaatatacgc aacgtcgtcg tccgtggcta tcgcaactat cgaataaaaa acaatcgaat | 180 |
| acgggtcgtg tacaaccgtc gaaacgtaaa ccgctaccgc cgctaccgcc gtcggaagta | 240 |
| gcggaagaaa aaatacaagt aaaagcgcta tatgattttc taccgcgtga accgtgtaat | 300 |
| ctagcgctac gtcgtgcgga agaatatcta atactagaaa aatataatcc gcattggtgg | 360 |
| aaagcgcgtg atcgtctagg taatgaaggt ctaataccgt cgaattatgt aacggaaaat | 420 |
| aaaataacga atctagaaat atatgaatgg tatcatcgta atataacgcg taatcaagcg | 480 |
| gaacatctac tacgtcaaga atcgaaagaa ggtgcgttta tagtacgtga ttcgcgtcat | 540 |
| ctaggttcgt atacgatatc ggtatttatg ggtgcgcgtc gttcgacgga agcggcgata | 600 |
| aaacattatc aaataaaaaa aaatgattcg ggtcaatggt atgtagcgga acgtcatgcg | 660 |
| tttcaatcga taccggaact aatatggtat catcaacata atgcggcggg tctaatgacg | 720 |
| cgtctacgtt atccggtagg tctaatgggt cgtgtctac cggcgacggc gggttttcg | 780 |
| tatgaaaaat gggaaataga tccgtcggaa ctagcgttta taaagaaat aggttcgggt | 840 |
| caatttggtg tagtacatct aggtgaatgg cgttcgcata tacaagtagc gataaaagcg | 900 |
| ataaatgaag gttcgatgtc ggaagaagat tttatagaag aagcgaaagt aatgatgaaa | 960 |
| ctatcgcatt cgaaactagt acaactatat ggtgtatgta taaacgtaa accgctatat | 1020 |
| atagtaacgg aatttatgga aaatggttgt ctactaaatt atctacgtga aaataaaggt | 1080 |
| aaactacgta aagaaatgct actatcggta tgtcaagata tatgtgaagg tatgaatat | 1140 |
| ctagaacgta atggttatat acatcgtgat ctagcggcgc gtaattgtct agtatcgtcg | 1200 |
| acgtgtatag taaaaatatc ggattttggt atgacgcgtt atgtactaga tgatgaatat | 1260 |
| gtatcgtcgt ttggtgcgaa atttccgata aaatggtcgc cgccggaagt atttctattt | 1320 |
| aataaatatt cgtcgaaatc ggatgtatgg tcgtttggtg tactaatgtg gaagtattt | 1380 |
| acggaaggta aaatgccgtt tgaaaataaa tcgaatctac aagtagtaga agcgatatcg | 1440 |
| gaaggttttc gtctatatcg tccgcatcta gcgccgatgt cgatatatga agtaatgtat | 1500 |
| tcgtgttggc atgaaaaacc ggaaggtcgt ccgacgtttg cggaactact acgtgcggta | 1560 |
| acggaaatag cggaaacgtg gtag | 1584 |

<210> SEQ ID NO 10
<211> LENGTH: 1083
<212> TYPE: DNA
<213> ORGANISM: Artificial sequence
<220> FEATURE:
<223> OTHER INFORMATION: Mutated MAPK gene

<400> SEQUENCE: 10

| | |
|---|---|
| atggcggcgg cggcggcggc gggtgcgggt ccggaaatgg tacgtggtca agtatttgat | 60 |
| gtaggtccgc gttatacgaa tctatcgtat ataggtgaag gtgcgtatgg tatggtatgt | 120 |

```
tcggcgtatg ataatgtaaa taaagtacgt gtagcgataa aaaaaatatc gccgtttgaa      180
catcaaacgt attgtcaacg tacgctacgt gaaataaaaa tactactacg ttttcgtcat      240
gaaaatataa taggtataaa tgatataata cgtgcgccga cgatagaaca aatgaaagat      300
gtatatatag tacaagatct aatggaaacg gatctatata aactactaaa aacgcaacat      360
ctatcgaatg atcatatatg ttattttcta tatcaaatac tacgtggtct aaaatatata      420
cattcggcga atgtactaca tcgtgatcta aaaccgtcga atctactact aaatacgacg      480
tgtgatctaa aaatatgtga ttttggtcta gcgcgtgtag cggatccgga tcatgatcat      540
acgggttttc taacggaata tgtagcgacg cgttggtatc gtgcgccgga aataatgcta      600
aattcgaaag gttatacgaa atcgatagat atatggtcgg taggttgtat actagcggaa      660
atgctatcga atcgtccgat atttccgggt aaacattatc tagatcaact aaatcatata      720
ctaggtatac taggttcgcc gtcgcaagaa gatctaaatt gtataataaa tctaaaagcg      780
cgtaattatc tactatcgct accgcataaa aataaagtac cgtggaatcg tctatttccg      840
aatgcggatt cgaaagcgct agatctacta gataaaatgc taacgtttaa tccgcataaa      900
cgtatagaag tagaacaagc gctagcgcat ccgtatctag aacaatatta tgatccgtcg      960
gatgaaccga tagcggaagc gccgtttaaa tttgatatgg aactagatga tctaccgaaa     1020
gaaaaactaa aagaactaat atttgaagaa acggcgcgtt ttcaaccggg ttatcgttcg     1080
tag                                                                   1083

<210> SEQ ID NO 11
<211> LENGTH: 13
<212> TYPE: DNA
<213> ORGANISM: Artificial sequence
<220> FEATURE:
<223> OTHER INFORMATION: ISRE common sequence
<220> FEATURE:
<221> NAME/KEY: misc_feature
<222> LOCATION: (7)..(7)
<223> OTHER INFORMATION: n stands for any base
<220> FEATURE:
<221> NAME/KEY: misc_feature
<222> LOCATION: (8)..(8)
<223> OTHER INFORMATION: n stands for any base
<220> FEATURE:
<221> NAME/KEY: misc_feature
<222> LOCATION: (13)..(13)
<223> OTHER INFORMATION: n stands for any base

<400> SEQUENCE: 11
agaaacnnaa can                                                         13
```

METHOD FOR SUPPRESSING CELL GROWTH

CROSS-REFERENCE TO RELATED PATENT APPLICATION

The present application claims priority under Japanese Patent Application 2008-311106, filed on Dec. 5, 2008, the entire contents of which are hereby incorporated by reference.

TECHNICAL FIELD

The present invention relates to a method for suppressing the growth of a target cell by inducing the expression of a protein in the target cell. The present invention further relates to a method for preparing a virus-resistant transformant by introducing DNA into a target cell. Still further, the present invention relates to a vector employed in these methods and a target cell growth-suppressing agent comprising this vector as an active component, and to a virus growth-suppressing agent and a growth-preventing agent.

BACKGROUND ART

In principle, the expression of a protein proceeds along the pathway of transcribing the information in DNA coding for the protein into mRNA, and then polymerizing the amino acids specified by the nucleotide information in the transcribed mRNA to synthesize (translate) the protein. The amino acids are specified in units of three nucleotides (referred to as "codons" hereinafter) in the mRNA nucleotide information. Each codon corresponds to a single amino acid. However, in some cases, two to six codons each correspond to the same amino acid. For example, there are six codons that correspond to the amino acid leucine in human beings: CUG, UUA, UUG, CUU, CUC, and CUA.

Codons are not necessarily uniformly employed in a target cell. Normally, their use is somewhat lopsided. The frequency of use of each type of codon among the multiple codons specifying a single amino acid (the "use frequency" hereinafter) exhibits diversity in biological species through the process of evolution (Nonpatent References 1 to 3). The use frequency of codons correlates positively with the tRNA concentration within the cell. The concentration of tRNA corresponding to high usage codons is high, and the genes constituted by high usage codons exhibit high levels of expression (Nonpatent References 4 to 8). The fact that the concentration of tRNA corresponding to low usage codons is low in cells has come to be understood. In particular, the concentration in cells of the tRNA corresponding to the codon with the lowest use frequency in terms of a genome (referred to as the "rear codon" hereinafter) is the lowest among the cellular concentrations of the tRNA of all codons (Nonpatent References 9 and 10). Since the use frequency of codons varies between biological species, for example, the expression level of a human-derived gene will decrease in *Escherichia coli* relative to what it is in a human cell (Nonpatent Reference 10).

Thus far, the method of adjusting the level of expression of a protein within the cell of a living organism of the same or different species has been reported as a technique that involves replacing the codons constituting the mRNA translating a protein with codons of different use frequencies (Patent References 1 and 2). Further, a method of changing the properties of a cell by adjusting the expression level of a protein that is expressed by the cell using the methods described in Patent References 1 and 2 has been reported (Patent Reference 3). For example, it is possible to suppress the growth of a cell by the method described in Patent Reference 3.

Patent Reference 1; Japanese Patent Unexamined Publication No. 2001-509388
Patent Reference 2; Japanese Patent Unexamined Publication No. 2006-500927
Patent Reference 3; Japanese Patent Unexamined Publication No. 2006-506986
Nonpatent Reference 1; Sharp, P. M. & Matassi, *Curr Opin Genet Dev.* 4, 851-860 (1994).
Nonpatent Reference 2; Bulmer, M. *Genetics,* 149, 897-907 (1991).
Nonpatent Reference 3; Sharp, P. M., Stenico, M., Peden, J. F. & Lloyd, A. T., *Biochem, Soc. Trans.* 21, 835-841 (1993).
Nonpatent Reference 4; Ikemura, T., *J. Mol. Biol.* 151, 389-409 (1981).
Nonpatent Reference 5; Ikemura, T., *Mol. Biol. Evol.* 2, 13-34 (1985).
Nonpatent Reference 6; Sharp, P. M. & Li, W., *J. Mol. Evol.* 24, 28-38 (1986).
Nonpatent Reference 7; Anderson, S. G. E. & Kurland, C. G., *Microbiol. Rev.* 54, 198-210 (1990).
Nonpatent Reference 8; Bennetzen, J. L. & Hall, B. D., *J. Biol. Chem.* 257, 3026-3031 (1982).
Nonpatent Reference 9; Fumiaki, Y., Yoshiki, A., Akira, M., Toshimichi, I. & Syozo, O., *Nucleic Acids Res.* 19, 6119-6122 (1991).
Nonpatent Reference 10; Makrides, S. C., *Microbiol Rev.* 60, 512-538 (1996).

The entire contents of Nonpatent References 1 to 10 are hereby incorporated by reference.

SUMMARY OF THE INVENTION

Problem to be Solved by the Invention

However, in the method described in Patent Reference 3, the cells that can serve as targets of suppression (referred to as "target cells" hereinafter) and the types of proteins that are expressed are limited. Further, in the method described in Patent Reference 3, the criteria for selecting the codons that are contained in the protein so as to suppress cell growth are unclear; this method requires a variety of preparatory testing.

Accordingly, the first object of the present invention is to provide a method for suppressing the growth of a target cell that does not limit the target cell or the type of protein to be expressed and that does not require preparatory testing to determine which codons are contained in the protein that is to be expressed. The second object of the present invention is to provide a method for preparing a virus-resistant transformant by applying the above method. The third object of the present invention is to provide a vector permitting the implementation of these methods, a target cell growth-suppressing agent comprising this vector as an active component, a virus growth-suppressing agent, and a growth-preventing agent.

Means of Solving the Problem

The present inventors conducted extensive research. As a result, they established the hypothesis that by causing at least a portion of a three-nucleotide chain that is complementary to a codon that is contained in a region coding for an arbitrary protein to be a three-nucleotide chain that is complementary to a codon of low use frequency in a target cell, incorporating DNA containing this region into the target cell, and inducing expression of the protein coded for by this DNA in the target cell, it should be possible to generate a deficiency in the tRNA corresponding to the codon of low use frequency in the target cell, suppress the expression in the target cell of a protein that is essential to bioactivity, and ultimately, suppress growth of the target cell.

Based on this hypothesis, when the present inventors used green fluorescent protein (GFP) as the arbitrary protein, utilized a database of the use frequencies of codons currently having entries for more than 30,000 species, employed at least a portion of a region coding for GFP as a three-nucleotide chain complementary to a synonymous codon of low use frequency in *E. coli* and yeast, introduced DNA containing this region into *E. coli* and yeast, and induced expression of the GFP coded for by the DNA in *E. coli* and yeast, they successfully suppressed the growth of *E. coli* and yeast.

In this method, since the protein to be expressed is any arbitrary protein, and since an existing database can be utilized to select the codon contained in the protein and the target cell, the target cell and the type of protein to be expressed are not limited, and no preparatory testing is required to determine the codon to be contained in the protein to be expressed.

The present inventors conducted further extensive research. They constructed a vector in which expression of the above DNA was controlled by a psp promoter, which is a promoter functioning during viral infections. They then prepared a transformant by introducing this vector into a target cell and infected the transformant with a virus. As a result, the present inventors discovered that the virus did not grow in the target cell into which the vector had been introduced. The present invention was devised based on this knowledge.

Accordingly, the present invention provides a method of suppressing the growth of a target cell, comprising the steps of:

incorporating DNA containing a region coding for an arbitrary protein into a target cell; and inducing expression of the protein coded for by the DNA in the target cell into which the DNA has been incorporated;

wherein the region of DNA contains a three-nucleotide chain, and the three-nucleotide chain is selected from among codons specifying at least a portion of the amino acids constituting the protein, and is complementary to at least a portion of codons having a use frequency of 0.2 or lower in the target cell.

In a desirable form of the method for suppressing the growth of a target cell of the present invention, the use frequency is 0.15 or lower.

In a desirable form of the method for suppressing the growth of a target cell of the present invention, the codon comprised of a three-nucleotide chain is a single type of codon for a single type of amino acid.

In a desirable form of the method for suppressing the growth of a target cell of the present invention, the "at least a portion of the amino acids" is at least three members selected from the group consisting of: alanine, arginine, glycine, isoleucine, leucine, proline, serine, threonine, and valine, and is preferably arginine, leucine, and valine.

In a desirable form of the method for suppressing the growth of a target cell of the present invention, the three-nucleotide chain is comprised of at least 80 three-nucleotide chains.

In a desirable form of the method for suppressing the growth of a target cell of the present invention, the DNA is DNA containing regions coding for a promoter of an interferon regulatory factor gene, an interferon gene promoter, an interferon-stimulated response promoter, or a phage shock protein (psp) promoter, and an arbitrary protein.

In a desirable form of the method for suppressing the growth of a target cell of the present invention, the DNA is inserted into a vector and introduced into the target cell.

Another aspect of the present invention is to provide a method for preparing a virus-resistant transformant comprising the steps of:

obtaining a transformant by introducing DNA containing regions coding for a promoter of an interferon regulatory factor gene, an interferon gene promoter, an interferon-stimulated response promoter, or a phage shock protein (psp) promoter, and an arbitrary protein into a target cell;

wherein the region of DNA contains a three-nucleotide chain, and the three-nucleotide chain is selected from among codons specifying at least a portion of the amino acids constituting the protein, and is complementary to at least a portion of codons having a use frequency of 0.2 or lower in the target cell.

In a desirable form of the method for preparing a virus-resistant transformant of the present invention, the use frequency is 0.15 or lower.

In a desirable form of the method for preparing a virus-resistant transformant of the present invention, the codon comprised of a three-nucleotide chain is a single type of codon for a single type of amino acid.

In a desirable form of the method for preparing a virus-resistant transformant of the present invention, the "at least a portion of the amino acids" is at least three members selected from the group consisting of: alanine, arginine, glycine, isoleucine, leucine, proline, serine, threonine, and valine.

In a desirable form of the method for preparing a virus-resistant transformant of the present invention, the "at least a portion of the amino acids" is arginine, leucine, and valine.

In a desirable form of the method for preparing a virus-resistant transformant of the present invention, the three-nucleotide chain is comprised of at least 80 three-nucleotide chains.

Another aspect of the present invention is to provide a vector containing DNA containing a region coding for an arbitrary protein in a state that can be expressed, wherein the region of the DNA contains a three-nucleotide chain; and the three-nucleotide chain is selected from among codons specifying at least a portion of the amino acids constituting the protein, and is complementary to at least a portion of the codons having a use frequency of 0.2 or lower in a target cell.

Another aspect of the present invention is to provide a vector into which can be inserted DNA containing a region coding for an arbitrary protein, wherein the region of DNA contains a three-nucleotide chain; and the three-nucleotide chain is selected from among codons specifying at least a portion of the amino acids constituting the protein, and is complementary to at least a portion of the codons having a use frequency of 0.2 or lower in a target cell.

In a desirable form of the vector of the present invention, the use frequency is 0.15 or lower.

In a desirable form of the vector of the present invention, the codon comprised of a three-nucleotide chain is a single type of codon for a single type of amino acid.

In a desirable form of the vector of the present invention, the "at least a portion of the amino acids" is at least three members selected from the group consisting of: alanine, arginine, glycine, isoleucine, leucine, proline, serine, threonine, and valine.

In a desirable form of the vector of the present invention, the "at least a portion of the amino acids" is arginine, leucine, and valine.

In a desirable form of the vector of the present invention, the three-nucleotide chain is comprised of at least 80 three-nucleotide chains.

Another aspect of the present invention is to provide a target cell growth-suppressing agent comprising the vector of the present invention as an active component.

In a desirable form of the vector of the present invention, the DNA is DNA containing regions coding for a promoter of an interferon regulatory factor gene, an interferon gene promoter, an interferon-stimulated response promoter, or a phage shock protein (psp) promoter, and an arbitrary protein.

Another aspect of the present invention is to provide a virus growth-suppressing agent or growth-preventing agent comprising the vector of the present invention as an active component.

Effect of the Invention

By means of the method for suppressing the growth of a target cell of the present invention, since the protein to be expressed can be any arbitrary protein and since an existing database can be used to select the codon or target cell, neither the type of target cell nor the protein to be expressed is limited, and the growth of the target cell or the growth of a virus that has infected the target cell can be suppressed without preparatory testing to determine the codons contained in the protein to be expressed. By means of the method for preparing a virus-resistant transformant of the present invention, neither the type of target cell nor the protein to be expressed is limited, and a virus-resistant transformant can be prepared without preparatory testing to determine the codons to be contained in the protein to be expressed. The vector of the present invention can be employed in the above methods of the present invention, and can contain a target cell growth-suppressing agent or virus growth-suppressing agent and growth-preventing agent as active components. For example, the method for suppressing the growth of a target cell and the target cell growth-suppressing agent of the present invention can suppress the growth of human cells or suppress the growth of a virus that has infected human cells.

In all forms of the present invention, the gene expression system can be utilized in accordance with the normal bioactivity of cells. Accordingly, it is difficult for the target cell or virus to escape the growth- and growth-preventing effects based on the present invention by undergoing mutation. Accordingly, it can be said that the methods and growth-suppressing and growth-preventing agents of the present invention suppress the growth of cells or viruses with high efficiency. infection by and the spreading of viruses is one of the issues of greatest concern in the world. The methods and drugs that are currently known to control viruses have as their goals to afford protection from just specific viruses, and are ineffective for preventing infection by and the spreading of mutated viruses and other closely related viruses. By contrast, the methods and growth-suppressing and growth-preventing agents of the present invention suppress the synthesis of viral proteins in the cell, and thus effectively prevent the spreading of viruses (that is, all viruses, including mutations) using the protein synthesizing system of the host cell. Still further, the methods and growth-suppressing and growth-preventing agents of the present invention can be applied to various living organisms by combining promoters that respond to viral infection. As a result, it is also possible to suppress the growth of cells infected with viruses. By applying the methods and growth-suppressing and growth-preventing agents of the present invention, suppression of the growth of micro-organisms that have been cultured in bioreactors and the like can also be anticipated.

MODES OF CARRYING OUT THE INVENTION

Figure 1:
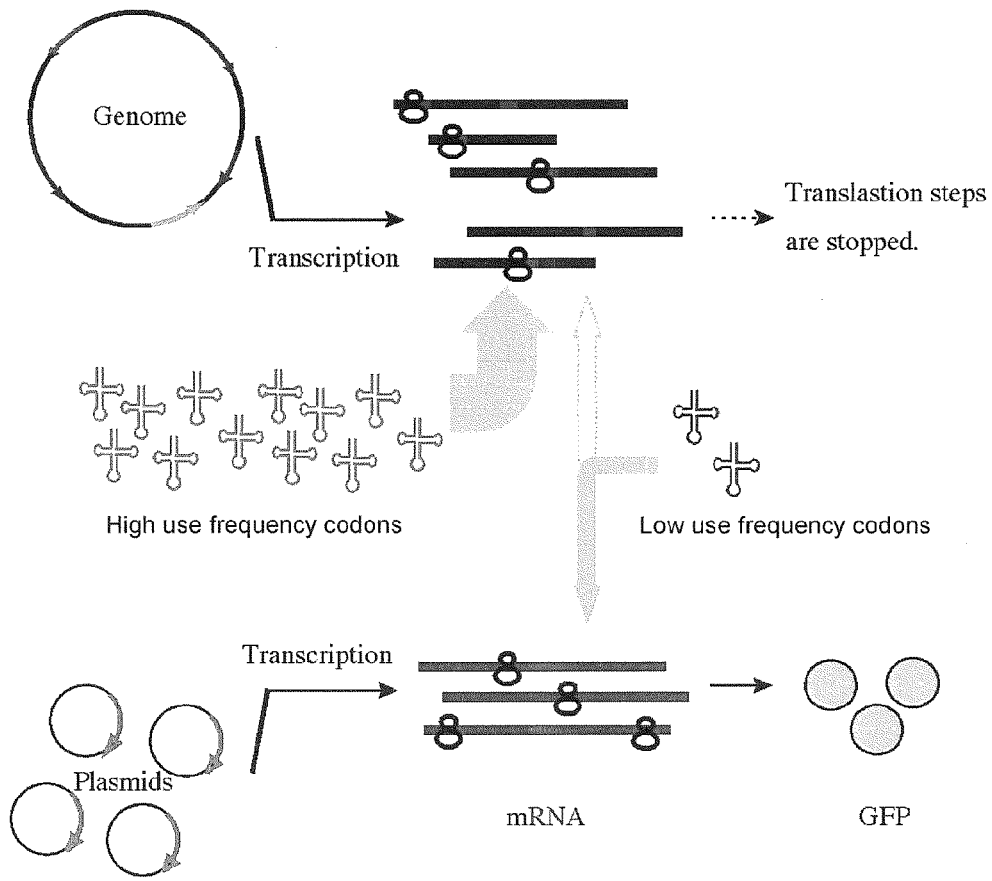
FIG. 1 shows a schematic of the suppressing of the translation of a nonspecific gene by means of a gene constituted by low usage codons.

The method for suppressing the growth of a target cell of the present invention suppresss the growth of a target cell by introducing DNA containing a region coding for an arbitrary protein into the target cell, and inducing expression of the protein coded for by the DNA in the target cell into which the DNA has been introduced.

The region coding for the arbitrary protein contains a three-nucleotide chain that is selected from among codons specifying at least a portion of the amino acids constituting the arbitrary protein, and is complementary to at least a portion of codons having a use frequency of 0.2 or lower in the target cell. More specifically, the region coding for the arbitrary protein is comprised of a three-nucleotide chain that is complementary to two or more codons of one, two, or more types specifying two or more amino acids of one, two, or more types constituting the arbitrary protein. However, all or part of the three-nucleotide chain is a three-nucleotide chain that is complementary to codons corresponding to tRNA the concentration of which is estimated to be low in the target cell, such as codons with a prescribed use frequency that is at or below a prescribed level in the target cell, desirably 0.2 or lower, preferably 0.18 or lower, and more preferably, 0.15 or lower.

The term "codon" is synonymous with the term that is commonly employed in this field of art. For example, it refers to a three-nucleotide chain that is contained in mRNA and has information specifying an amino acid constituting a protein. One codon specifies one amino acid, but a single amino acid can be specified by one or multiple codons. For example, in humans, there are six codons that specify leucine: UUA, UUG, CUU, CUC, CUA, and CUG. Accordingly, the term "three-nucleotide chain complementary to a codon," in the example of a codon specifying leucine, would refer to AAT, AAC, GAA, GAG, GAT, or GAC, which are the three-nucleotide chains that are complementary to the above codons specifying leucine.

The use frequency of each of the codons specifying an amino acid normally differs depending on the target cell. For example, in human cells, the use frequency of the codons specifying leucine is as follows: 0.08 for UUA, 0.13 for UUG, 0.13 for CUU, 0.20 for CUC, 0.07 for CUA, and 0.40 for CUG. Accordingly, in human cells, among codons specifying leucine, the use frequency of CUA is the highest, and the use frequency of UUA is the lowest. The use frequency of a codon varies with the living organism and with the cell. For example, this can be checked at the URL: http://www.kazusa.or.jp/codon/. Table 1 shows the use frequencies of the codons of *Homo sapiens* as examples of codon use frequencies. The fraction in Table 1 denotes use frequency.

TABLE 1

*Homo sapiens* [gbpri]: 93487 CDS's (40662582 codons)

fields: [triplet][amino acid][fraction][frequency: per thousand]([number])

| UUU | F | 0.46 | 17.6 (714296) | UCU | S | 0.19 | 18.2 (618711) | UAU | Y | 0.44 | 12.2 (495695) | UGU | C | 0.46 | 10.6 (430311) |
|---|---|---|---|---|---|---|---|---|---|---|---|---|---|---|---|
| UUC | F | 0.64 | 20.3 (924692) | UCC | S | 0.22 | 17.7 (718992) | UAC | Y | 0.56 | 15.3 (622407) | UGC | C | 0.54 | 12.6 (513028) |
| UUA | L | 0.08 | 7.7 (311881) | UCA | S | 0.16 | 12.2 (496448) | UAA | * | 0.30 | 1.0 (40286) | UGA | * | 0.47 | 1.6 (63237) |
| UUG | L | 0.18 | 12.9 (525686) | UCG | S | 0.06 | 4.4 (179419) | UAG | * | 0.24 | 0.8 (32109) | UGG | W | 1.00 | 13.2 (535595) |
| CUU | L | 0.13 | 13.2 (536515) | CCU | P | 0.29 | 17.5 (713233) | CAU | H | 0.42 | 10.9 (441711) | CGU | R | 0.06 | 4.5 (184609) |
| CUC | L | 0.20 | 19.6 (796638) | CCC | P | 0.32 | 19.8 (804620) | CAC | H | 0.59 | 15.1 (613713) | CCC | R | 0.16 | 10.4 (423516) |
| CUA | L | 0.07 | 7.2 (290761) | CCA | P | 0.28 | 16.9 (688038) | CAA | Q | 0.27 | 12.8 (501911) | CGA | R | 0.11 | 6.2 (250760) |
| CUG | L | 0.40 | 39.6 (1611801) | CCG | P | 0.11 | 6.9 (281570) | CAG | Q | 0.73 | 34.2 (1391973) | CGG | R | 0.20 | 11.4 (464485) |
| AUU | I | 0.36 | 16.0 (650473) | ACU | T | 0.25 | 13.1 (533609) | AAU | N | 0.47 | 17.0 (689701) | AGU | S | 0.15 | 12.1 (433429) |
| AUC | I | 0.47 | 20.8 (846466) | ACC | T | 0.36 | 18.9 (768147) | AAC | N | 0.53 | 19.1 (776603) | AGC | S | 0.24 | 15.5 (731383) |
| AUA | I | 0.17 | 7.5 (304565) | ACA | T | 0.28 | 15.1 (614523) | AAA | K | 0.43 | 24.4 (993621) | AGA | R | 0.21 | 12.2 (494682) |
| AUG | M | 1.00 | 22.0 (896005) | ACG | T | 0.11 | 6.1 (246105) | AAG | K | 0.57 | 31.9 (1295568) | AGG | R | 0.21 | 12.0 (436463) |

TABLE 1-continued

Homo sapiens [gbpri]: 93487 CDS's (40662582 codons)

fields: [triplet][amino acid][fraction][frequency: per thousand]([number])

| GUU | V | 0.18 | 11.0 (448607) | GCU | A | 0.27 | 18.4 (750096) | GAU | D | 0.46 | 21.8 (385429) | GGU | G | 0.16 | 10.8 (437126) |
| GUC | V | 0.24 | 14.5 (588138) | GCC | A | 0.40 | 27.7 (1127679) | GAC | D | 0.54 | 25.1 (1020595) | GGC | G | 0.34 | 22.2 (903565) |
| GUA | V | 0.12 | 7.1 (287712) | GCA | A | 0.28 | 16.8 (643471) | GAA | E | 0.42 | 29.0 (1177632) | GGA | G | 0.25 | 16.5 (669873) |
| GUG | V | 0.46 | 28.1 (1143534) | GCG | A | 0.11 | 7.4 (299495) | GAG | E | 0.68 | 39.6 (1609975) | GGG | G | 0.25 | 16.5 (669768) |

Coding GC 52.27% 1st letter GC 55.72% 2nd letter GC 42.54% 3rd letter GC 58.55%
Genetic code 1: Standard In the present specification, without adhering to any specific theory or conjecture, the mechanism behind the method for suppressing the growth of a cell in the present invention is presumed to be as follows.

The present inventors conducted extensive research into the phenomenon whereby cell growth is suppressed by the expression of a foreign protein in a target cell. Therein, the present inventors discovered that the growth of a target cell could be suppressed by inducing the expression of an arbitrary protein coded for by mRNA containing a codon with a low use frequency in the target cell. The present inventors presume that this is because expression of the arbitrary protein monopolizes tRNA corresponding to the codon of low use frequency in the target cell, thereby suppressing proteins relating to bioactivity, such as cell growth, that are coded for by mRNA containing the codon of low use frequency.

FIG. 1 is a conceptual diagram that illustrates the above presumption. tRNA corresponding to low usage codons is monopolized by the mRNA of a mutant GFP gene containing numerous low usage codons (arrows pointing downward in FIG. 1). As a result, the expression of other genes in the cell stops at the translation stage (arrows pointing upward in FIG. 1) because of a lack of tRNA corresponding to low usage codons, ultimately suppressing bioactivity within the cell, such as growth.

The present inventors believe that this presumption is supported by the facts that the concentration of tRNA corresponding to high usage codons is high and the concentration of tRNA corresponding to low usage codons is low within cells. The present inventors conducted further extensive research, and as anticipated, discovered that it was possible to suppress the growth of the target cell by inducing the expression in a target cell of a protein coded for by DNA containing some portion in the form of codons with a use frequency at or below a prescribed level in the target cell. The present invention was devised on that basis. The strategy of the method for suppressing the growth of a target cell of the present invention may resemble a "Denial of Service (DoS) attack" on a computer system or network. The strategy of controlling biological activity by means of a DoS attack on a biosystem has been conceived of and attempted for the first time by the present inventors.

Based on this presumption, it is desirable for there to be one to three codons, preferably one to two codons, and more preferably, one codon of lower than or equal to a prescribed use frequency in the target cell for a single type of amino acid to efficiently monopolize the tRNA that is anticipated to be of low concentration in the target cell. As a specific example of when using one type of codon with a use frequency of 0.15 or lower in the target cell for an amino acid, one codon can be selected from the group consisting of UUA (use frequency: 0.08), UUG (use frequency: 0.13), CUU (use frequency 0.13), and CUA (use frequency: 0.07) when the target cell is a human cell and the codon with a use frequency of 0.15 or lower in the target cell is leucine.

When the number of codons specifying a single amino acid is large, there tend to be differences in the use frequency of the codons. Accordingly, the amino acid that is specified by codons of lower than or equal to a prescribed use frequency in the target cell is desirably an amino acid that is specified by four or six codons. Depending on the type of target cell, alanine, arginine, glycine, isoleucine, leucine, proline, serine, threonine, and valine are preferred, and arginine, leucine, and valine are of greater preference.

The number of types of amino acids specified by codons of lower than or equal to a prescribed use frequency in the target cell is desirably three or more, preferably four or more, more preferably five or more, and still more preferably, six or more when DNA repairs such as frame shift mutations are taken into account.

Since the use frequency of codons varies with the type of target cell, the number and type of codons with lower than or equal to a prescribed use frequency in the target cell can be suitably adjusted based on the species of living organism. A region containing a three-nucleotide chain that is complementary to each of the codons specifying five arginines, 11 leucines, and 14 valines, with use frequencies that are lower than or equal to a prescribed use frequency in the target cell, is a desirable example of a region coding for an arbitrary protein. However, it is not limited to it.

Since the use frequency of codons varies with the type of target cell, the number of the three-nucleotide chains complementary to codons of lower than or equal to a prescribed frequency use in a target cell can be suitably adjusted by means of the species of living organism or the type of cell. However, so long as it permits suppression of the growth of the target cell by the expression of an arbitrary protein in the target cell, this number is not specifically limited. For example, this number is desirably 80 or higher, preferably 90 or higher, and more preferably, 100 or higher.

The arbitrary protein that is expressed in the target cell is not specifically limited. For example, it can be any protein that is endogenous or exogenous in the target cell. For example, it is desirably a protein that is expressed in the normal activity of the target cell, and preferably one that is homeostatically expressed in the target cell. The phrase "the normal activity of the target cell" does not limit, but includes, the common biological activities of the target cell. Examples are DNA replication and repair, the uptake and discharge of nutritional substances, the expression of enzymes, cell growth, the attacking and expelling of foreign cells, germination, and spore formation, but there is no limitation thereto. Proteins that are homeostatically expressed in the target cell include proteins that are expressed by housekeeping genes. The phrase "proteins that are expressed by housekeeping genes" refers to proteins that are expressed by almost all cells, such as proteins the expression of which is induced unexpectedly by housekeeping genes, and proteins the expression of which is induced by unknown substances, but whose expression levels have no effect on the level of expression of housekeeping genes. Examples of housekeeping genes are β-actin and glyceraldehyde-3-phosphate dehydrogenase (GAPDH), but there is no limitation thereto. When the target gene is a human gene, SEQ. ID NOS. 7 and 8 of the SEQUENCE LISTING are desirable specific examples of the β-actin gene and GAPDH gene, respectively, that can be employed in the methods of the present invention.

In expression in the target cell, the arbitrary protein can be in a functional state or in a non-functional state. For example, when the arbitrary protein is an enzyme having a specific catalytic function, the enzyme that is expressed within the target cell can be capable or incapable of performing the catalytic function.

For example, when the characteristic to be suppressed is clear, a protein that is expressed by an expression-inducing gene is desirably employed as the arbitrary protein. An expression-inducing gene affords the advantage of facilitating estimation of the level of expression because its expression profile has been thoroughly analyzed. However, it is necessary to consider the possibility that expression may be induced by unknown expression-inducing substances and the like. Examples of proteins that are expressed by expression-inducing genes are tyrosine kinase, which is induced by immunoglobulin and cytokine, and oxidative stress-induced mitogen activated protein kinase (MAPK), but there is no limitation thereto. When the target gene is a human gene, SEQ. ID NOS. 9 and 10 of the SEQUENCE LISTING are desirable specific examples of the tyrosine kinase gene and MAPK gene, respectively, that can be employed in the methods of the present invention.

When the target cell is a cancer cell, examples of the arbitrary protein are proteins that are highly expressed in the target cell, such as epidermal growth factor receptor (EGFR), platelet-derived growth factor receptor (PDGFR), vascular endothelial growth factor receptor (VEGFR), and other tyrosine kinase receptor proteins; Src-family, Syk-ZAP-70 family, BTK family, and other cytoplasmic tyrosine kinases; Ras protein and other regulatory GTPases; Raf kinase, cyclin-dependent kinases, and other cytoplasmic serine/threonine kinases and their regulatory subunits; signal transmission system adapter proteins; and myc, ets, and other transcription factors.

To monitor the expression of the arbitrary protein, a reporter protein such as green fluorescent protein (GFP), DsRed, or a luciferase is desirably spliced onto the N-terminus or C-terminus of the arbitrary protein for use in the form of a fused protein. Further, these reporter proteins can be employed alone as the arbitrary protein. Since the expression of GFP has been confirmed in various cells, it is a desirable example of a reporter protein. When the target cell is *E. coli*, SEQ. ID NOS. 1 and 2 of the SEQUENCE LISTING are desirable specific examples of suitable GFP genes that can be employed in the method for suppressing the growth of a target cell in the present invention. When the target cell is yeast, SEQ. ID NO. 5 of the SEQUENCE LISTING is a desirable specific example of a suitable GFP gene that can be employed in the method for suppressing the growth of a target cell of the present invention.

Expression of the arbitrary protein in the target cell is normally achieved by way of transcribing DNA containing the region coding for the arbitrary protein in the target cell into mRNA serving as template. That is, expression of the arbitrary protein is achieved by transcribing DNA information in the target cell into mRNA, which is a central dogma of molecular biology, and then translating the RNA information into a protein. When the target cell is a eukaryote, in the course of translating the mRNA information into a protein, various processing such as splicing can be conducted.

Since the tRNA concentration changes with the state of activity of the target cell and since the expression level of the arbitrary protein is impacted by the number and type of synonymous codons contained in the mRNA coding for the arbitrary protein, the expression level of the arbitrary protein is not specifically limited. For example, a level of 0.018 pg/cell or higher is desirable, 0.030 pg/cell or higher is preferred, and 0.050 pg/cell or higher is of greater preference.

When the arbitrary protein is GFP, the expression level of the arbitrary protein can be determined by the following method.

The cultured cells are separated by centrifugation (8,000 rpm, 1 minute, 4° C.), rinsed with PBS buffer solution (75 mM sodium phosphate, 67 mM NaCl (pH 7.4)), and suspended in PBS buffer solution. This suspension is then employed as a sample in GFP measurement. The GFP expression level is measured in 30,000 cells using a Becton Dickinson FACSCalibur flow cytometer.

Any DNA synthesis method that is known to date can be employed without limitation as the method of synthesizing the DNA containing the region coding for the arbitrary protein. Specific examples of DNA synthesis are chemical synthesis methods based on the triester phosphate method or the amidate phosphate method conducted on the basis of information in the nucleotide sequence of DNA containing the region coding for the protein or the amino acid sequence of a wild-type arbitrary protein (J. Am. Chem. Soc., 89, 4801 (1967); ibid. 91, 3350 (1969); Science, 150, 178 (1968); Tetrahedron Lett., 22, 1859 (1981); ibid. 24, 245 (1983)); methods of introducing a site-specific mutation into the nucleotide sequence of DNA containing a region coding for a wild-type arbitrary protein (Methods in Enzymology, 154, 350, 367-382 (1987); ibid. 100, 468 (1983); Nucleic Acids Res., 12, 9441 (1984); Course 1, Cont'd Biochemistry Experiments, "Genetic Research Methods II," comp. by the Japanese Biochemical Society, p. 105 (1986)); other genetic engineering methods; and combinations of these methods. For example, DNA can also be chemically synthesized by the phosphoramidite method or the triester method in a commercial automated oligonucleotide synthesizer. Still further, a complementary strand can be synthesized from a single-stranded product obtained by chemical synthesis and annealed to the strand under suitable conditions, or a complementary strand can be copied using DNA polymerase with a suitable primer sequence to obtain a double-stranded fragment.

The DNA containing the region coding for the arbitrary protein can be directly introduced into the nucleus of the target cell, particularly into a chromosome. However, it is normally inserted into a suitable vector and then introduced into the target cell. The vector can be one that can be independently copied, or one that is combined into a chromosome of the target cell in the course of introduction into the target cell, and then copied only with the chromosome. It is desirably an expression vector. Specific examples of expression vectors are: plasmid vectors, phage vectors, and virus vectors. The DNA containing the region coding for the arbitrary protein is functionally linked with elements necessary for transcription (such as promoters) in the expression vector. A promoter is a DNA sequence that exhibits transcription activity in the target cell, and can be suitably selected based on the type of the target cell.

Specific examples of plasmid vectors are pTAK, pIKE, pTSMb1, pYES2, pAUR112, pET21a, pRSETA, pCR8, pBR322, pBluescript II SK(+), pUC18, pCR2.1, pLEX, pJL3, pSW1, pSE280, pSE420, pHY300PLK, pTZ4, pC194, pUB110, pHV14, TRp7, YEp7, and pBS7. Specific examples of phage vectors are Charon4A, Charon21A, EMBL3, EMBL4, λgt10, λgt11, λZAP, ρ11, φ1, and φ105. Specific examples of virus vectors are animal-borne viruses such as retroviruses, lentiviruses, adenoviruses, and vaccinia viruses; and insect-borne viruses such as baculoviruses. These are not specifically limited so long as they are capable of establishing a host-vector expression system with the target cell.

The promoter is not specifically limited other than that it be capable of functioning in the target cell. In $E.$ $coli$, examples are promoters such as the lactose operon (lac) and the tryptophan operon (trp) and the tac promoter. In $Bacillus$ $subtilis$, examples are promoters of the maltogenic amylase gene of $Bacillus$ $stearothermophilus$, the α-amylase gene of $Bacillus$ $licheniformis$, and the BAN amylase gene of $Bacillus$ $amyloliquefaciens$. In yeast, examples are the promoters of the alcohol dehydrogenase gene (ADH), acid phosphatase gene (PHO), galactose gene (GAL), and glyceraldehyde-3-phosphate dehydrogenase gene (GPD). In fungi, examples are promoters of the α-amylase gene (amy) and cellobiohydrolase I gene (CBHI), ADH3 promoter, and tpiA promoter. In mammalian cells, examples are the SV40 promoter, MT-1 (metallothionein gene) promoter, and the major late promoter of adenovirus 2. In insect cells, examples are the polyhedrin promoter, P10 promoter, basic protein promoter of $Autographa$ $californica$ polyhedrosis, Baculovirus immediate-early gene 1 promoter, and Baculovirus 39K delayed-early gene promoter. Additional examples are the lambda-phage $P_R$ and $P_L$ promoters. Promoters that function based on prescribed forms of stress, such as cell carcinogenesis, abnormal gene expression, and viral infection are desirable. Promoters that function based on viral infection will be described further below.

The expression vector can contain a selection marker. For example, drug-resistance markers and nutrient-requirement markers can be employed as selection markers. Specific examples of selection markers are, when the target cell is a bacterium, ampicillin-resistance genes, kanamycin-resistance-genes, tetracyclin-resistance genes, and other antibiotic-resistance genes. When the target cell is yeast, examples are the dihydrofolic acid reductase (DHFR) gene, $Shizosaccaromyces$ $pombe$ TPI gene, tryptophan synthesis gene (TRP1), uracil synthesis gene (URA3), and leucine synthesis gene (LEU2). When the target cell is a fungus, examples are hygromycin-resistance gene (Hyg), bilanafos-resistance gene (Bar), and nitrate reductase gene (niaD).

The expression vector is desirably spliced into a DNA sequence required for expression of the arbitrary protein, such as a promoter, enhancer, ribosome-binding site, secretion signal sequence, terminator, and the like in an appropriate order.

Examples of non-expression vectors are ribosomes, artificial lipid vesicles, dendrimers, and other high-polymer compounds. In that case, commercial introduction reagents (lipofectin, lipofectamine, DMRIE-C(made by Invitrogen), Metafectene, DOTAP (made by BioTex), Tfx reagent (made by Promega)) are desirably employed.

Any of the methods known thus far can be employed without limit as the method of introducing the vector into the target cell. It suffices to select a method that is suited to the target cell and vector. For example, the protoplast method, electroporation method, calcium phosphate method, lipofection method, and method employing calcium ions can be employed.

In addition to the above, any known method of introducing the DNA containing the region coding for the arbitrary protein, method of introducing a vector into the target cell, or the like can be employed without limitation. For example, this can be conducted by the methods described in Molecular Cloning: A Laboratory Manual, $2^{nd}$ Ed., Cold Spring Harbor Laboratory, Cold Spring Harbor, N.Y., 1989 (abbreviated to "Molecular Cloning, $2^{nd}$ Ed." hereinafter), Current Protocols in Molecular Biology, Supplement 1 to 38, John Wiley & Sons (1987-1997) (abbreviated to Current Protocols in Molecular Biology" hereinafter), and the like.

The target cell is not limited other than that it permits the introduction of DNA containing a region coding for the arbitrary protein. This includes the cells of all living organisms, aggregates thereof in the form of tissues and organs, and portions thereof. The concept includes living organisms having target cells such as humans, dogs, cats, horses, swine, sheep, rabbits, guinea pigs, mice, rats, and other mammals; birds; reptiles; amphibians; fish; plants; and microorganisms such as bacteria and viruses. Of these, animal cells that readily produce cancer cells, desirably mammal cells, and preferably human cells, are employed.

Examples of target cells in the form of cells, tissue, and organs are the cerebellum, cerebral cortex, pituitary gland, neurons, neuroblasts, mononuclear blood cells, oocytes, embryonic cells, liver, pancreas, lungs, intestinal tissue, lymphocytes, pancreas βcells, lipocytes, liver cells, fibroblasts, mucosal epithelial cells, hematopoietic stem cells, epidermal cells, central nerve, peripheral nerves, bone marrow, lymph vessels, blood vessels, heart (cardiac muscle and valves), spleen, esophagus, stomach, colon, kidneys, bladder, uterus, ovaries, testacles, diaphragm, muscle, sinew, skin, eyes, nose, trachea, tongue, and lips, as well as portions thereof.

The method for suppressing the growth of target cells of the present invention can be applied to the prevention and/or treatment of diseases thought to be caused by anomalies in cell cycles, such as cancer, autoimmune disease, neurodegeneration, and diseases based on developmental anomalies and chromosomal anomalies. Examples of cancer are stomach cancer, colon cancer, breast cancer, lung cancer, esophageal cancer, prostate cancer, liver cancer, kidney cancer, bladder cancer, skin cancer, uterine cancer, brain tumors, osteosarcoma, and bone marrow tumors. Examples of autoimmune disease are chronic rheumatoid arthritis, multiple sclerosis, myasthenia gravis, thyroiditis, polymyositis, systemic lupus erythematosus, Behcet's disease, and Basedow's disease. Examples of neurodegeneration are Alzheimer's disease and Parkinson's disease. Examples of diseases based on developmental and chromosomal anomalies are genetic diseases, gamete disease, embryopathy, fetopathic abortion, Down's syndrome, and Turner's syndrome. The above diseases are given by way of example, and not limitation. The method of the present invention can be applied with the goal of preventing the onset of the above diseases, or with the goal of preventing the worsening of symptoms or alleviating symptoms in patients who have contracted the above diseases.

The suppression of the growth of the target cell can be confirmed by detecting the absence or presence of target cell growth by the usual known methods of determining cell growth. Examples of methods of determining cell growth are: the method of culturing the target cell in a suitable medium to obtain a culture product, sampling the culture product, and observing the sampling solution under a microscope; the method of applying the sampling solution to a suitable solid medium to form colonies; the method of measuring the absorbance (for example, OD660 nm) of the sampling solution; the method of measuring the activity of genes or enzymes relating to growth in sampling solution; the method of drying the sampling solution and weighing the dry bacterial weight; and methods combining the above. For convenience, the method of measurement by absorbance is desirable.

The DNA containing the region coding for the arbitrary protein can contain a promoter or sequence functioning in response to viral infection, such as an interferon regulatory factor gene promoter, an interferon gene promoter, an interferon-stimulated response promoter, or a phage shock protein (psp) promoter. A desirable specific example of these promoters is a psp promoter, which is expressed during phage infection.

Interferon regulatory factors are a family of transcription regulatory factors that target regions known as IRF-E and ISRE that are present in the promoter regions of many interferon inducing genes. They are abbreviated as IRFs. IRFs are factors that exhibit high homology with terminal amino acid portions. As of today, 10 types have been reported: IRF1 to IRF10. For example, IRF1 functions as a cancer-suppressing gene, and plays important roles in suppressing cell growth and aptosis. IRF3 is said to regulate expression of the interferon β gene that is activated by signals from TLR3 and TLR4 and viral infection. IRF7 is said to be the principal regulatory factor of the interferon α-dependent immune response. Interferon regulatory factor gene promoters are promoters that regulate the transcription of the genes of interferon regulatory factors. A desirable example is the promoter that regulates the transcription of the IRF3 gene, which is activated by viral infection.

An interferon gene promoter is a promoter that regulates the transcription of an interferon gene. Desirable examples are promoters that regulate the transcription of the interferon α, β, and γ genes.

An interferon-stimulated response element is a DNA sequence of 12 to 15 nucleotides that is important in inducing the expression of interferon-stimulated responses present in the transcription-regulating region of a group of genes (interferon-inducing genes) that are induced by interferon α/β and γ stimulation. It is abbreviated as ISRE. The common sequence among ISREs is AGAAACNNAACAN (A/G) (SEQ. ID NO.: 11 in the SEQUENCE LISTING). Thus, ISREs are not specifically limited other than that they have the sequence recorded in SEQ. ID NO.: 11 in the SEQUENCE LISTING. A promoter that has this interferon-stimulated response element is an interferon-stimulated response promoter. The IRF family of transcription factors (IRF-2, ICSBP, and the like), including the transcription factors ISGF3 (a complex containing IRF-9) and IRF-1 that are induced by interferon stimulation, bind to this site and are thought to control transcription.

For more detailed information on interferon regulatory factor gene promoters, interferon gene promoters, and interferon-stimulated response promoters, the known literature, such as Muramatsu et al., eds., Dictionary of Molecular Biology, 2nd ed. (2008), pp. 95-96; Paun A, Pith P M, Biochimie, 2007 89(6-7): 744-53; Ozato K, Tailor P, Kubota T, J Biol Chem. 2007 282(28): 20065-9; Hiscott J, Pitha P, Genin P, Ngyuen H, Heylbroeck C, Mamane Y, Algarte M, Lin R, J Interferon Cytokine Res. 1999 19(1):1-13, can be consulted. The entire contents of these references are hereby incorporated by reference.

Generally, when an immunocyte is infected by a virus, sensor proteins are activated that are responsible for detecting viral infection in cells. The sensor proteins bind to other factors, becoming transcription activation factors. The transcription activation factors induce the expression of interferon regulatory factors having an activation factor binding sequence containing the common sequence IRF3, resulting in the production of interferon. When interferon is produced, the immunocytes are activated and proteins having antiviral activity are produced.

When the DNA containing the region coding for an arbitrary protein contains the above promoter or sequence functioning in response to viral infection, the region coding for an arbitrary protein is functionally spliced downstream from the promoter or the like functioning in response to virus infection. When DNA containing a region coding for an arbitrary protein that has been functionally spliced with a promoter or the like functioning in response to viral infection is introduced into a target cell and the target cell is infected by a virus, the arbitrary protein will be expressed in the target cell. Thus, not only will the growth of the target cell be suppressed, but the growth of the virus can be suppressed.

Figure 14:
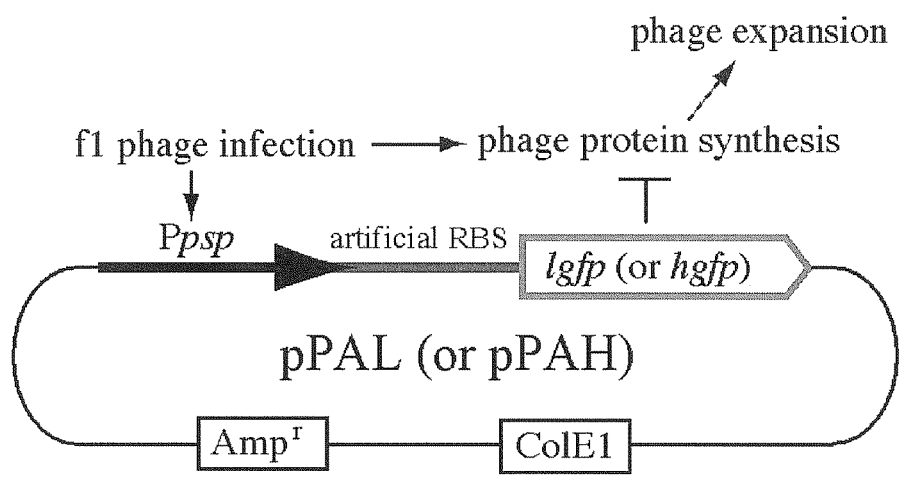
FIG. 14 shows a schematic of the construction of a gene induction system based on phage infection.

A desirable example of DNA containing a region coding for an arbitrary protein and a promoter functioning in response to viral infection is the gene induction system depicted in FIG. 14. The vector pPAL described in FIG. 14 contains ColE1 and an ampicillin-resistance gene. Further, the nucleotide sequence (lgfp gene) of a region coding for GFP, which is an arbitrary protein into which a nucleotide sequence that is complementary to a codon with a use frequency lower than or equal to a prescribed level has been substituted, has been spliced downstream from the psp operon modification promoter. When a cell having pPAL is infected by a virus (phage), it expresses lgfp (LGFP). The expression of lgfp (LGFP) suppresses the phage protein synthesizing system. As a result, the growth of both the target cell and the phage is suppressed. In the pPAH shown in FIG. 14, which is employed as a control, hgfp is disposed in place of the lgfp (LGFP) of pPAL.

A gene induction system that is induced by viral infection can be constructed by using any of the usual, known methods without limitation. The gene induction system depicted in FIG. 14 is an example. Any system that is known to date, such as a promoter that is activated by viral infection, a subsequent Rep binding site (RBS), replication starting point, or the like, can be employed without limitation. Various antibiotic-resistance genes can be employed as set forth above. However, when the gene induction system is used in a mammalian cell, it is desirable to exclude antibiotic-resistance genes.

A low number of copies of the promoter during viral infection presents the possibility of not being able to suppress the viral protein synthesizing system. A high number of copies present the possibility of the vector being eliminated from the cell. For example, 5 to 10,000 copies are desirable, 10 to 700 copies are preferred, 20 to 500 copies are of greater preference, and 20 to 200 copies are of still greater preference.

A method of confirming viral growth, a method of confirming the growth of the infected cell, or a combination of the two can be used to confirm the suppression of viral growth. The plaque method described below is an example of a method of confirming viral growth.

A virus solution is prepared by removing the insoluble cells from a culture solution containing viruses and cells by centrifugation (8,000 rpm, 10 minutes, 4° C.) and filtering the solution through a membrane filter with a pore size of 0.2 µm. Host cells suited to the virus are admixed to the virus solution, after which the mixed solution is applied to a solid medium suited to viral growth. The suitable solid medium is stacked in layers and the virus and host cells are cultured at a suitable temperature. Following culturing, the number of plaques that form (pfu) is determined and the concentration of virus is calculated.

In addition to the above diseases, the method for suppressing the growth of a target cell of the present invention is effective against diseases thought to be caused by viruses, such as viral hepatitis (types A, B, C, E, G, and TTV), adenovirus infection, influenza, viral pneumonia, viral bronchitis, Herpes infection, (Herpes simplex, EB virus (infectious mononucleosis), Herpes Zoster), polio, AIDS (HIV infection), adult T-cell leukemia (ATL), papilloma, measles, rubella, Exanthema subitum, Erythema infectiosum, viral encephalitis, viral meningitis, cytomegalovirus infection, mumps, chickenpox, rabies, viral enteritis, viral pericarditis, Coxsackie virus, Echo virus infection, hemorrhagic fever with renal syndrome, Lassa fever, and SARS virus infection. The above diseases have been indicated by way of example and not limitation. The method for suppressing the growth of a target cell of the present invention can be applied with the goal of preventing the onset of the above diseases, or with the goal of preventing the deterioration of symptoms or alleviating symptoms in patients who have contracted the above diseases.

A further form of the present invention provides a method for preparing a virus-resistant transformant, comprising the steps of introducing DNA containing a promoter functioning in response to viral infection and a region coding for an arbitrary protein into a target cell to obtain a transformant.

The method for preparing a virus-resistant transformant permits the preparation of a transformant that is resistant to viruses, and as a result, permits the suppression or reduction of various diseases caused by viral infection. A transformed plant is a desirable example of the transformant. The method for preparing a virus-resistant transformant of the present invention permits the preparation of transformed plants having resistance to such viruses as plant-transmitted viruses in the form of nematode-borne viruses such as: Nepoviruses: Arabis mosaic virus, grapevine leafroll-associated virus, tomato black ringspot virus, strawberry ringspot virus, tomato ringspot virus, and tobacco ringspot virus; Tobraviruses: pea early browning virus, tobacco rattle virus, and pepper ringspot virus; fungus-borne viruses: cucumber green mottle virus, cucumber yellow necrotic virus, melon necrotic spot virus, red clover necrotic mosaic virus, pumpkin wilt virus, tobacco yellow blotch necrosis satellite virus, lettuce big vein virus, pepper yellow vein virus, beet necrotic yellow vein virus, beet soil-borne virus, oat stripe mosaic virus, Nanking bean mottle virus, potato mop top virus, rice stripe necrosis virus, soil-borne wheat streak mosaic virus, barley mild mosaic virus, barley yellow dwarf virus, oat mosaic virus, rice necrosis mosaic virus, wheat streak mosaic virus, and wheat yellow mosaic virus; viruses propagating through root damage such as: Tobamoviruses: tobacco mosaic virus, tomato mosaic virus, cucumber green mottle mosaic tobamo virus, cucumber fruit mottle mosaic virus, cucumber green mottle mosaic virus, ondogrossam ringspot virus, paprika mild mottle virus, pepper mild mottle virus, *Plantago asiatica* mosaic virus, tobacco mild green spot mosaic virus; viruses with unknown propagation pathways: watercress yellow spot virus, broad bean necrotic wilt virus, peach rosette mosaic virus, sugarcane streak mosaic virus; virus families: Caulimoviridae, Geminiviridae, Circoviridae, Reoviridae, Taruchichi family viruses, Bromoviridae, Comoviridae, Potyviridae, Tombusviridae, Sekui family viruses, Closteroviridae, and Luteoviridae; and viruses of the genera Tobamovirus, Tobravirus, Potexvirus, Carlavirus, Allexivirus, Capillovirus, Foveavirus, Trichovirus, grape viruses, Furovirus, Pecluvirus, Pomovirus, Benyvirus, Hordeivirus, Sobemovirus, Marafivirus, Tymovirus, Idaeovirus, Ourumivirus, and Umbravirus.

A further form of the present invention is a vector containing the DNA containing a region coding for an arbitrary protein in a state that can be expressed, a vector into which can be inserted DNA containing a region coding for an arbitrary protein, and a target cell growth-suppressing agent containing these vectors as active components. A still further form of the present invention is a vector containing the DNA containing a promoter functioning in response to viral infection or the like and a region coding for an arbitrary protein in a state that can be expressed, a vector into which can be inserted DNA containing a promoter functioning in response to viral infection or the like and a region coding for an arbitrary protein, and a virus growth-suppressing and growth-preventing agent containing these vectors as active components. The target cell growth-suppressing agent and virus growth-suppressing agent and growth-preventing agent of the present invention will on occasion be referred to as the "drugs of the present invention."

The quantity of the active component vector that is contained in the drugs of the present invention is not specifically limited other than that it permits the growth of the target cell and the suppression and prevention of the growth of the virus. However, by way of example, it is desirably 80 to 100% relative to each agent. So long as the drug of the present invention contains an effective quantity of the vector, it can be used in either solid or liquid form. One or more pharmacologically acceptable carriers or additives can be compounded therein to prepare a solid or liquid medicinal composition.

Examples of medicinal compositions that are suited to oral administration are tablets, capsules, powders, fine grains, granules, liquids, and syrups. Examples of medicinal compositions that are suited to non-oral administration are injections, drops, suppositories, inhalation agents, eyedrops, nosedrops, ointments, creams, patches, transdermally absorbed agents, and transmembrane absorption agents. Examples of formulation additives that can be employed in the preparation of these medicinal compositions are: excipients such as lactose and oligosaccharides, disintegrators, disintegrating adjuvants, binders, gloss-imparting agents, coating agents, coloring materials, diluting agents, bases, solvents, solvent adjuvants, isotonic agents, pH-regulating agents, stabilizers, propellants, and thickening agents. These can be suitably selected by a person having ordinary skill in the art based on the form of the medicinal composition. They can also be employed in combinations of two or more.

When employing the drugs of the present invention to prevent or treat cancer or a viral disease, the target cell and virus growth-suppressing agent of the present invention is generally desirably not employed alone, but in combination with a suitable anti-carcinogen or antiviral agent.

An example of a desirable form of the drugs of the present invention is an injection. As an injection, the drug normally essentially does not contain nonaqueous solvents (or water-soluble organic solvents). The medium can be dissolved or diluted with a solvent that is essentially comprised of water. A further example of a desirable form of the drugs of the present invention is a freeze-dried formulation (freeze-dried injection). Such a freeze-dried agent can be readily prepared as an injection by being dissolved in at least one liquid or solvent selected from among infusions including water for injection (injection-use distilled water), electrolytic solutions (physiological saline or the like), or the like, and nutrient infusions. A common known container such as a glass container or a plastic container can be employed. The drugs of the present invention are incorporated in a quantity of 0.01 weight part or more, desirably 0.1 to 10 weight part, per 100 weight parts of injection contents.

The dosage and frequency of administration of the drugs of the present invention are not specifically limited, and can be suitably selected based on conditions such as the age, weight, and sex of the patient, as well as the type and severity of the diseases, and whether the goal is prevention or treatment. For example, when being administered non-orally, the quantity of active component is desirably 0.01 mg to 10,000 mg, preferably 0.1 mg to 1,000 mg, and more preferably 0.1 mg to 100 mg, per day for an adult. Such a dosage can be divided up into several daily administrations.

In addition to use as the above medicinal drugs, the drugs of the present invention can be used as topical medicinal drugs, cosmetic products, functional foods, nutritional supplements, foods, and beverages. When employed as topical medicinal drugs or cosmetic products, combined use as needed with the various supplemental agents that are commonly employed in the fields of art relating to topical medicinal products and cosmetics is possible. When employed as functional foods, nutritional supplements, foods, or beverages, combined use as needed with the additives commonly employed in foods, such as sweeteners, fragrance materials, seasonings, preservatives, storage agents, bactericidal agents, and antioxidants, is possible. The drugs of the present invention can also be employed in the form of solutions, suspensions, syrups, granules, creams, pastes, jellies, and the like as desired, or molded as needed for use. The proportion that is contained therein is not specifically limited, and can be suitably selected based on the use objective, form employed, and quantity employed.

The present invention is described in greater detail below through embodiments. However, the present invention is not limited to the embodiments given below.

Embodiment 1

Experimental Materials and Methods
(1) Bacterial strains, phages, and drugs employed, and plasmid construction Artificial GFP genes lgfp (LGFP), and hgfp were synthesized by designing gene sequences based on a codon use frequency database (Nakamura, Y., Gojobori, T. & Ikemura, T., (2000), Nucleic Acids Res. 28, 292) on the basis of the amino acid sequence of the gfpmut3 gene, and relying on GenScript (Piscataway N.J., USA). The DNA sequences of lgfp (LGFP) and hgfp are recorded in the DDBJ database under Registration Nos. AB304879 and AB30487. Deletion mutant genes lgfp (LGFP) 41, lgfp (LGFP) 42, and lgfp (LGFP) 43 had 75%, 50%, and 25% of the length from the N-terminus of the lgfp (LGFP) gene, respectively, and were obtained by PCR amplification using the lgfp (LGFP) gene as template. The CAI value of the artificial deletion mutant genes were calculated using the site with the following URL: http://www.evolvingcode.net/codon/cai/ cai.php#146. All of the plasmids employed in the bacterial experiments were constructed (14, 29, 47) by standard cloning techniques using pTAK, plKE, and pTSMb1 plasmids (donated by Prof. J. J. Collins (Boston University, MA, USA)) as parts. Plasmids pHGFP, pLGFP, pLGFPΔ1, pLGFPΔ2, and pLGFPΔ3 were constructed by positioning hgfp (lgfp, lgfp (LGFP) Δ1, lgfp (LGFP) Δ2, and lgfp (LGFP) Δ3), respectively, downstream from the Ptrc promoter of pTAK132. pYEG, pLGFP1, and pLGFP2 were constructed by first positioning yEGFP, lgfp (LGFP), and hgfp genes downstream from the PGAL promoter of pYES2 (Invitrogen), obtaining the pGAL-various gfp genes-CYC1TT region by PCR, and cloning it in pAUR112 (Takara). plΔNG was constructed by incorporating a tetR suppressing gfpmut3 region cut out of plKE107 into pLGFPΔ1. pHΔNG was constructed by switching hgM1 with 25% deletion from the C-terminus of hgfp with the lgfp (LGFP) Δ1 of plΔNG. pPAL and pPAH were constructed by replacing pLGFP and the Lacl-PL-Ptrc regions of pHGFP with a psp promoter obtained by PCR from *E. coli* AK1. All PCR was conducted with Pyrobest DNA polymerase (Takara). *E. coli* MACH1 (Invitrogen: F-φ80 (lacZ), ΔM15, ΔlacX74, hsdR (rK−(mK+)), ΔrecA1398, endA1, tonA) was employed in gene cloning and in the GFP expression experiments. *E. coli* K-12 XL-10 (Clontech; deoR, endA1, gyrA96, hsdR 17 (rk−m−k+), recA1, relA 1, supE44, thi-1, Δ (lacZYA-argF) U169, φ80 ΔlacZ, ΔM15, FλPN25/tetR, Placiq/laci, Spr) was used to check the effect on growth of GFP expression in relA mutant strain. *E. coli* AK4, a random deletion mutant strain obtained from AK1, was employed in phage infection experiments (Kobayashi, H. et al., (2004), Proc. Natl. Acad. Sci. USA 101, 8414-8419). Phage T4 (NBRC20004) and T7 (NBRC20007) were purchased from NITE Biological Resource Center (Kazesa, Japan). Random phage (NCIMB10451) and Phages f1 (NCIMB13926) and MS2 (NCIMB10108) were purchased from National Collections Industrial, Food and Marine Bacteria (Aberdeen, UK). *S. cerevisiae* YPH499 (MATa, his3-, Δ200, leu2-Δ1 lys2-801, trp1-, Δ ade2-101 ura3-52) was used in GFP expression experiments in eukaryotes (Sikorski, R. S. & Herter, P., (1989), Genetics 122, 19-27). All of the plasmid DNA sequences constructed with the artificially synthesized gfp gene are recorded in the Supplemental Information.
(2) Growth Conditions and Chemical Products Employed
All of the *E. coli* strains were cultured in LB medium (Difco) at 37° C. and 160 rpm, adding 100 g/mL of ampicillin (SIGMA) as needed. The growth of *E. coli*. was measured by the turbidity (OD660) at 660 nm and the number of colonies formed (CFUs). When inducing expression with Ptrc and Ptet promoters, IPTG (SIGMA) or anhydrotetracycline (ACROS Organics) was added to the medium. *S. cerevisiae* was cultured in YPD medium (Difco) containing 0.5 g/mL of aureobasidin A (Takara). Culturing was conducted using YPGalactose medium containing 1% raffinose and 0.5 g/mL of aureobasidin A when inducing GFP expression. *S. cerevisiae* was shake-cultured at 200 rpm at 30° C.
(3) GFP Expression and Quantification
A 0.2% quantity of an *E. coli* culture solution that had been aerobically shake cultured at 37° C. overnight was transplanted to fresh ampicillin-containing LB medium and shake cultured. As needed, IPTG or aTc was added to the medium. The *E. coli* was centrifugally separated (8,000 rpm, 1 minute, 4° C.), rinsed with PBS buffer solution (75 mM sodium phosphate, 67 mM NaCl (pH 7.4)), suspended in PBS buffer solution, and employed as sample in GFP measurement. *S. cerevisiae* was aerobically cultured in YPD medium containing aureobasidin A for 24 hours at 30° C. The bacteria were collected and rinsed twice with YPGalactose medium, and the cells were suspended in aureobasidin A and raffinose-containing YPGalactose medium to an OD660 value of about 0.1. Samples for the measurement of GFP were prepared in the same manner as for E. coli. All of the GFP expression data were measured for 30,000 cells with a Becton Dickinson FACSCalibur flow cytometer.

(4) Measurement of Alkaline Phosphatase (ALP) Activity

The fungus body was collected from a 10 mL E. coli culture solution by centrifugal separation (8,000 rpm, 5 minutes, 4° C.), rinsed with deionized distilled water (DDW), and suspended in 0.3 mL of DDW. The fungus body was processed with 10% (v/v) toluene, mixed with 10 μL of fungus body suspension and 100 μL of p-nitrophenyl phosphate solution (Wako Chemical USA), and ALP reacted at 37° C. for 3 hours. The absorbance (A405) at 405 nm was measured and the ALP activity was calculated (Coleman, J. E., (1992), Annu. Rev. Biophys. Chem. 21, 441-483).

(5) Phage Experimentation

E. coli JM2.300 was employed as host for phages T7 and T4 and lambda-phage. E. coli AK4 was employed as host for phages MS2 and f1. Each of the phage solutions was prepared by removing by centrifugal separation (8,000 rpm, 10 minutes, 4° C.) the insoluble fungus body from a culture solution infected with the phage and passing the solution through a membrane filter with a pore size of 0.2 μm. Each of the phages and corresponding host bacteria were mixed in soft agar medium comprised of LB (T4 and T7), LB+0.2% maltose (lambda-phage), and ¼ LB (f1 and MS2) to which 0.8% agar had been added, the LB agar medium was stacked in layers and cultured at 37° C., the number of plaques that formed (pfu) was measured, and the phage concentration was calculated.

Experimental Results

Designing Artificial Genes for Suppressing the Growth of E. coli

Figure 2:
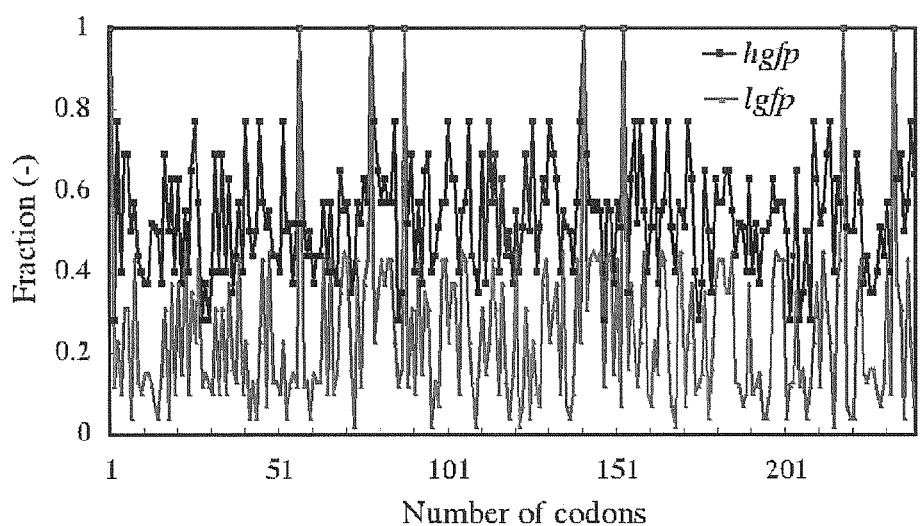
FIG. 2 shows the use frequencies of all codons constituting the gene hgfp (squares) and lgfp (LGFP) (triangles).

The gfpmut3 gene (green fluorescent protein gene, also referred to as "gfpmut3" hereinafter) was selected as a motif because of its lack of toxicity and ease of confirmation of expression in E. coli (Cormack, B. P., Valdivia, R. H., & Falkow, S., (1996), Gene 173, 33-38). Two artificial genes were synthesized based on the amino acid sequence of the gfpmut3 gene. One was a gene (lgfp) comprising the synonymous codon with the lowest usage frequency (lowest frequency codon) in an attempt to monopolize the tRNA corresponding to the low frequency codon. The other was a gene (hgfp) comprising the codon with the highest usage frequency (high frequency codon), and was employed as a control for lgfp (LGFP) (Table 2, FIG. 2). The use frequencies of the various codons were calculated based on the codon use database of E. coli W3110 at URL: http://www.kazusa.or.jp/codon/31.

TABLE 2

Codons of the hgfp and lgfp genes and their use frequencies in E. coli

| hgfp AA[b] Codon | Fraction[a] E. coli | Yeast | Num. | lgfp Codon | Fraction E. coli | Yeast | lgfp | Number lgfpΔ1 | lgfpΔ2 | lgfpΔ3 |
|---|---|---|---|---|---|---|---|---|---|---|
| Gly GGC | 0.41 | 0.19 | 23 | GGG | 0.14 | 0.12 | 23 | 19 | 14 | 9 |
| Lys AAA | 0.76 | 0.58 | 21 | AAG | 0.24 | 0.42 | 21 | 18 | 10 | 5 |
| Leu CUG | 0.51 | 0.11 | 18 | CUA | 0.03 | 0.14 | 18 | 11 | 8 | 6 |
| Asp GAA | 0.69 | 0.7 | 18 | GAC | 0.38 | 0.35 | 18 | 12 | 8 | 3 |
| Val GUG | 0.37 | 0.19 | 16 | GUA | 0.15 | 0.21 | 16 | 14 | 10 | 6 |
| Glu GAU | 0.62 | 0.65 | 15 | GAG | 0.31 | 0.3 | 15 | 12 | 9 | 5 |
| Thr ACC | 0.46 | 0.22 | 15 | ACA | 0.11 | 0.3 | 15 | 11 | 11 | 6 |
| Ile AUU | 0.49 | 0.46 | 13 | AUA | 0.06 | 0.27 | 13 | 10 | 3 | 2 |
| Asn AAC | 0.56 | 0.41 | 13 | AAU | 0.44 | 0.59 | 13 | 10 | 2 | 1 |
| Phe UUU | 0.57 | 0.59 | 12 | UUC | 0.43 | 0.41 | 12 | 11 | 9 | 3 |
| Tyr UAU | 0.54 | 0.56 | 12 | UAC | 0.46 | 0.44 | 12 | 9 | 6 | 1 |
| Pro CCG | 0.53 | 0.12 | 11 | CCC | 0.11 | 0.16 | 11 | 7 | 6 | 4 |
| Ser AGC | 0.28 | 0.11 | 9 | UCA | 0.11 | 0.21 | 9 | 6 | 4 | 3 |
| His CAU | 0.56 | 0.14 | 9 | CAC | 0.44 | 0.36 | 9 | 5 | 2 | 0 |
| Ala GCG | 0.37 | 0.11 | 9 | GCU | 0.16 | 0.38 | 9 | 5 | 4 | 1 |
| Gln CAG | 0.67 | 0.31 | 8 | CAA | 0.33 | 0.69 | 8 | 5 | 4 | 1 |
| Met AUG | 1 | 1 | 7 | AUG | 1 | 1 | 7 | 5 | 3 | 1 |
| Arg CGC | 0.41 | 0.06 | 6 | AGG | 0.02 | 0.21 | 6 | 5 | 3 | 0 |
| Cys UGC | 0.57 | 0.37 | 2 | UGU | 0.43 | 0.63 | 2 | 2 | 2 | 1 |

TABLE 2-continued

Codons of the hqfp and lqfp genes and their use frequencies in E. coli

| AA[b] | hgfp Codon | Fraction[a] E. coli | Yeast | Num. | lgfp Codon | Fraction E. coli | Yeast | lgfp | Number lgfpΔ1 | lgfpΔ2 | lgfpΔ3 |
|---|---|---|---|---|---|---|---|---|---|---|---|
| Trp | UGG | 1 | 1 | 1 | UGG | 1 | 1 | 1 | 1 | 1 | 1 |
| * | UAA | 0.64 | 0.47 | 1 | UAG | 0.05 | 0.23 | 1 | 1 | 1 | 1 |

[a] Fraction was based on *E. coli* W3110 and *S. cerevisiae* (yeast) as mentioned in Materials and Methods
[b] AA: Amino Acid The codon adaptation indexes (CAI) of gfpmut3, hgfp, and lgfp (LGFP) were 0.584, 1.00, and 0.0711, respectively (Carbone, A., Zinovyev, A. & Kepes, F., (2003), Bioinformatics, 19, 2005-2015). The homology of gfpmut3 relative to hgfp and lgfp (LGFP) in terms of its DNA sequence was 77% and 75%. No homology between lgfp (LGFP) and hgfp was found in the DNA sequences.

Figure 3:
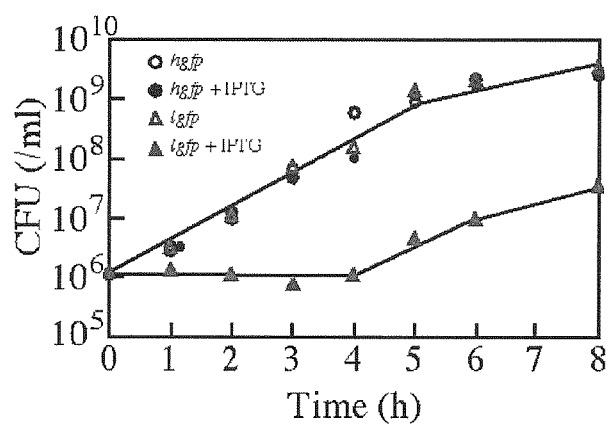
FIG. 3 shows the effect of hgfp (squares) and lgfp (LGFP) (triangles) expression on the growth of E. coli. The solid symbols and hollow white symbols in the figure indicate the results of the addition and non-addition, respectively, of a final concentration of 10 mM of IPTG to observe the effects of the expression of a mutant gfp gene.

Plasmids pHGFP and pLGFP were constructed with the lgfp (LGFP) or hgfp gene positioned in the downstream region from a Ptrc-2 promoter (suppressed by Laci) that was capable of being induced by isopropyl-13-D-thiogalactopyranoside (IPTG). pHGFP and pLGFP contained pBR322 ColE1 replication starting points and ampicillin-resistance genes (Gardner, T. S., Cantor, C. R. & Collins, J. J. (2000), Nature 403, 339-342). pLGFP and pHGFP were used to transform *E. coli*, and the effect of the inducement of the expression of lgfp (LGFP) and hgfp on *E. coli* growth was examined. The *E. coli* were aerobically cultured at 37° C. and the growth thereof was examined based on the number of colonies formed (CFU) and the turbulence at 660 nm (00660). When IPTG was added to the medium to induce the expression of lgfp (LGFP), no growth in the *E. coli* was observed four hours after the addition, followed by gradual growth. Conversely, induction of the expression of hgfp did not affect the growth of *E. coli* at all (FIG. 3). The medium 00660 exhibited the same growth curve as the CFU (data not disclosed).

Figure 4:
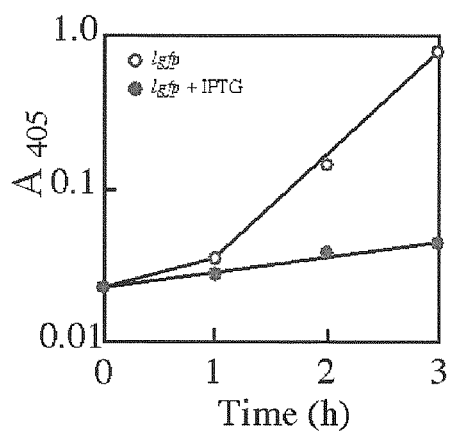
FIG. 4 shows the effect of lgfp (LGFP) expression on alkaline phosphatase (ALP) activity in E. coli. A final concentration of 10 mM IPTG was added to one culture solution recovered over time to induce lgfp (LGFP) expression (solid symbols). The other culture solution, to which no IPTG was added, served as a control (hollow white symbols). The various standard deviations, S.D., are contained in the symbols.
Figure 5:
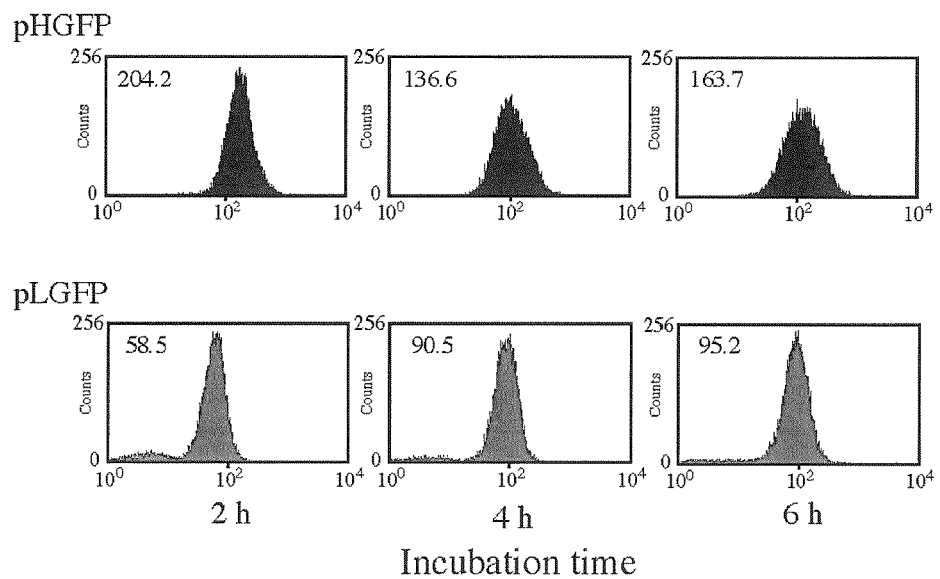
FIG. 5 shows the results of the expression of GFP by pHGFP or pLGFP as measured 2 to 6 weeks following IPTG induction. The numbers in the figure are the average values of the GFP expression level.
Figure 17:
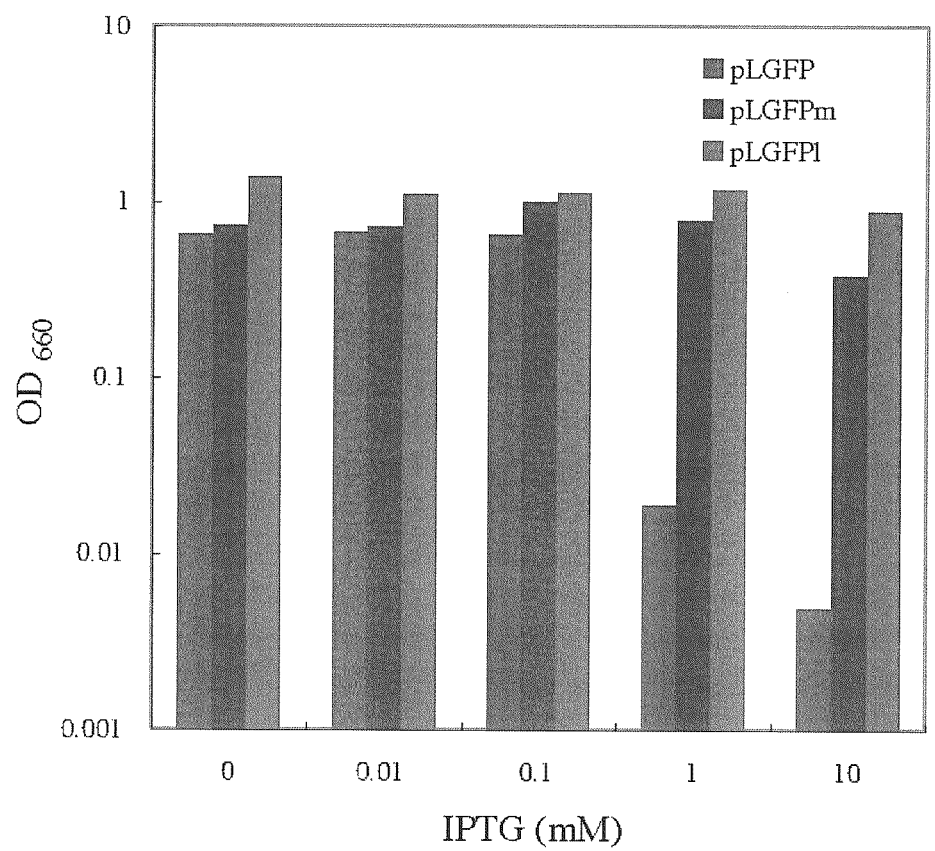
FIG. 17 shows the effect of the IPTG concentration and number of plasmid copies on growth suppression by lgfp (LGFP) induction. pLGFP, pLGFPm, and pLGFP1 respectively have ColE1, 15A, and SC101 replication starting points. Cell growth was measured based on the absorbance (OD660) of the culture product obtained by incubating *E. coli* cells containing the various plasmids for 4 hours at 37° C. and 160 rpm.

Evaluation of the Effect of Alkaline Phosphatase Activity on the Expression of Artificial Genes The effect of the induction of the expression of lgfp (LGFP) on the activity of alkaline phosphatase (ALP), one of the housekeeping genes of *E. coli*, was examined (Wilson, I. B., Dayan, J. & Cyr, K., (1964), J. Biol. Chem. 239, 4182-4185). The level of ALP activity in *E. coli* in which expression of the lgfp (LGFP) gene had been induced increased slightly during a period of halted growth of *E. coli*. Following three hours of culturing, the expression of lgfp (LGFP) suppressed ALP activity 2.8% relative to the control (FIG. 4). The halt in cell growth was presumed to have been caused by the suppression of the synthesis of various proteins in the same manner as ALP within the cell. The level of GFP expression by lgfp (LGFP) was about one third that of hgfp after two hours of culturing, and was half that of hgfp after six hours of culturing (FIG. 5). When 1 mM or less of IPTG was used to induce expression, no suppressing effect on growth due to expression of lgfp (LGFP) was observed. Several copies or 10 copies of the pLGFP plasmids containing 15A and sC101 replication start points were present within the cells, but no growth-suppressing effect was exhibited even when IPTG was added to a final concentration of 10 mM (FIG. 17). These results indicated that protein translated from the lgfp (LGFP) gene was not toxic to *E. coli*. Since various enzymes such as RNA polymerase did not suppress the enzymatic reactions, the increase in CFUs four hours later seemed to suggest an increase in tRNA content within the fungus body.

Evaluation of ppGpp Cascade Activity on the Expression of Artificial Genes

Figure 18:
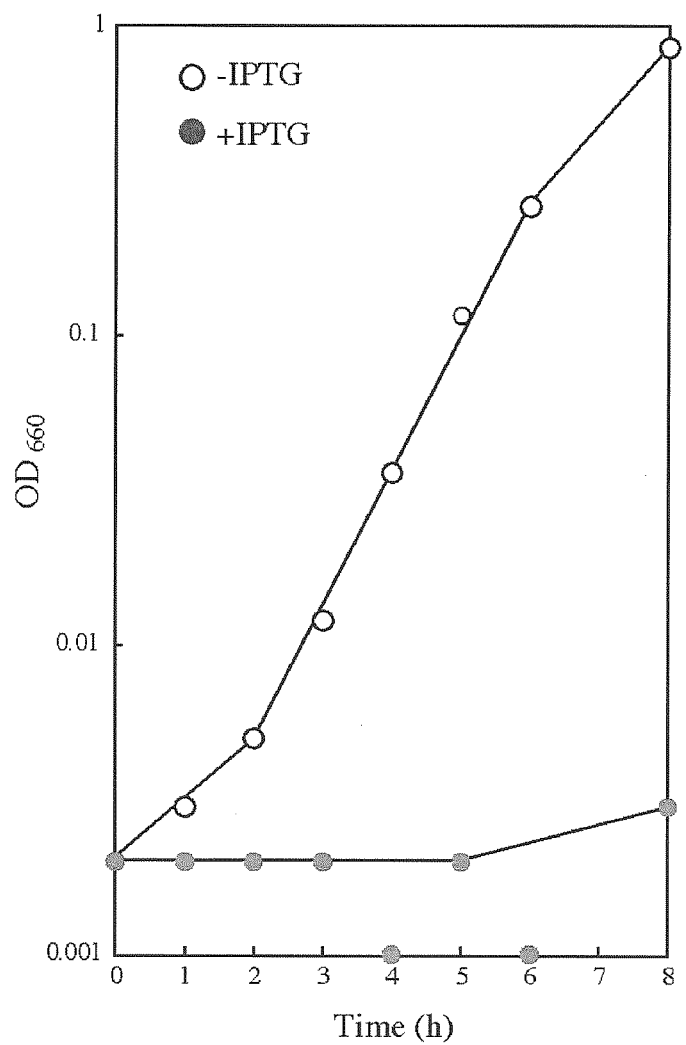
FIG. 18 shows the effect of lgfp (LGFP) induction in the growth of *E. coli* XL-10. Cell growth was measured at regular intervals based on the absorbance (OD660) at 660 nm of the culture product.

The halt in the synthesis of peptides due to a shortage of tRNA corresponding to low-frequency codons could potentially cause a false amino acid starvation signal to be sent in *E. coli*. There is also the possibility of activation of guanosine 5 3-bisdiphosphate (ppGpp), which suppresses growth (Magnussen, L. U., Farewell, A. & Nystrom, T., (2005), Trends Microbial. 13, 236-242). Accordingly, *E. coli* strain K-12 XL-10, in which the relA gene required for synthesizing ppGpp had been deleted, was employed to verify the growth-suppressing effect due to expression of lgfp (LGFP) (FIG. 18). Verification was conducted by aerobically culturing overnight at 37° C. *E. coli* strain XL-10 having pLGFP in LB medium containing ampicillin, diluting the culture to 1:500, and incubating the culture anew at 37° C. using LB medium that contained 10 mM of IPTG (black circles) and LB medium that did not contain IPTG (white circles). As a result, the expression of lgfp (LGFP) suppressed growth in the XL-10 strain, as well (FIG. 18). The suppression of growth caused by the lgfp (LGFP) gene was not related to the ppGpp network. This system was surmised that either a starvation signal was not generated, or synthesis of the protein required for the starvation signal was suppressed. These results suggested that in *E. coli*, tRNA corresponding to low frequency codons was monopolized, suppressing gene expression.

Figure 6:
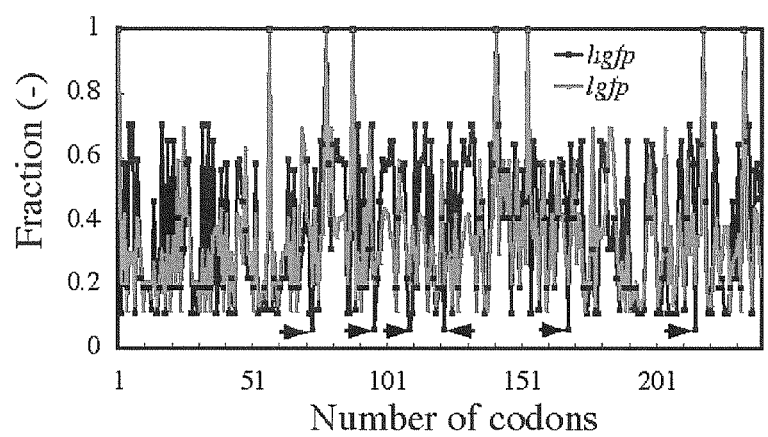
FIG. 6 shows the codon use frequency of hgfp (squares) and lgfp (LGFP) (triangles) in S. cerevisiae. The arrows in the figure indicate the arginine codon (CGC).
Figure 7:
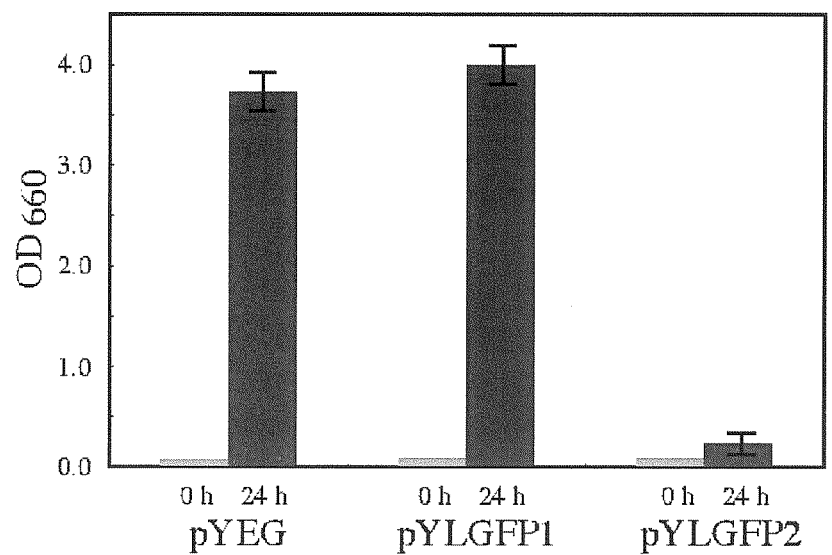
FIG. 7 shows the results of growth of S. cerevisiae containing pYEG, pYLGFP1, and pYLGFP2. The error bar in the figure indicates the standard deviation (n=3).
Figure 8:
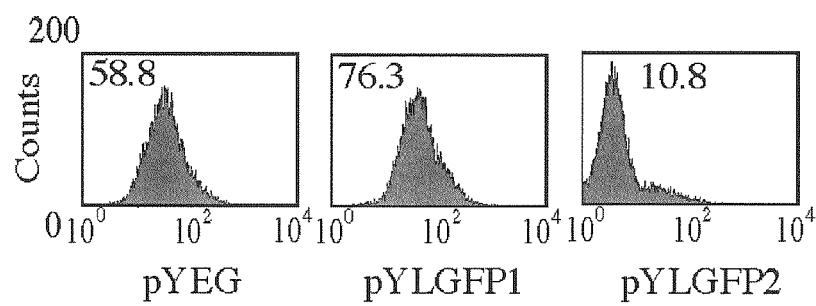
FIG. 8 shows the results of the expression of GFP by pYEG, pYLGFP1, and pYLGFP2. The numbers in the figure indicate the average values of the GFP expression level.

Suppressing the growth of eukaryotes with artificial genes Almost no difference in the translation process of mRNA has been found in the expression of genes in eukaryotes and prokaryotes. Accordingly, it was thought that the growth-suppressing effect of the high expression of artificial genes containing numerous low frequency codons might be observed in eukaryotes in the same manner as in prokaryotes. Yeast is an example of a model organism that is a eukaryote. A variety of host vector systems exist in yeast (Sikorski, R. S. & Herter, P., (1989), Genetics 122, 19-27). Additionally, in *S. cerevisiae*, lgfp (LGFP) and hgfp exhibit low CAIs of 0.0492 and 0.0522, respectively. Plasmids pYLGFP1 and pYLGFP2 were constructed with lgfp (LGFP) and hgfp positioned under the control of a promoter P-GAL that could be induced by galactose with an aureobasidin A-resistance gene in an *S. cerevisiae* vector. As a control, pYEG was constructed by replacing lgfp (LGFP) with the GFP gene (yEGFP) constructed by using high use frequency codons in yeast (Cormack, B. P. et al., (1997), Microbiology 143, 303-311). The CAIs of the artificially synthesized lgfp (LGFP) and hgfp genes were nearly identical. However, in *S. cerevisiae*, hgfp contained more rear codons than lgfp (LGFP). The low usage codon ratio of hgfp and lgfp (LGFP) was precisely the opposite of what it was in *E. coli* (Table 2). In the lgfp (LGFP) gene, there were only two low usage codons with frequencies of less than 0.15, 23 glycine codons (GGG), and 18 leucine codons (CUA). In hgfp, there were five types of low usage codons. In particular, there were six low usage arginine codons (CGC) that were positioned from the middle to the end of the hgfp gene (FIG. 6, arrows). The tRNA of Arg (CGC) is synthesized by a modification enzyme from the tRNA of AGC codons. (Auxilien, S., Crain, P. F., Trewyn, R. W. & Grosjean, H. H. (1996), J. Mol. Biol. 262, 437-458). To examine the effects of expression of each of the gfps, the S. cerevisiae containing pYLGFP1, pYLGFP2, or PYEG was cultured at 30° C. using YPGalactose medium (containing 1% raffinose) containing aureobasidin A (1 µg/ml). The various growth rates were measured as the 00660 of the solutions after 24 hours of culturing. As a result, suppressed growth was only observed in the S. cerevisiae containing pYLGFP2. This -suppressing effect was observed for a longer period than the suppressing effect of pLGFP observed in E. coli (FIG. 7). In the YPO medium in which GFP expression was not induced, all of the transformants exhibited 00660 turbidity levels in the media of 5.0 or higher after 24 hours of culturing (data not disclosed). The number of copies of pYLGFP2 in the yeast cell is reported to be about 10 (Sikorski, R. S. & Herter, P., (1989), Genetics 122, 19-27). That number is equal to the number of plasmids having 15A replication start points in E. coli. However, even when the replication start points of pLGFP were changed from ColE1 to 15A, no growth-suppressing effect due to expression of lgfp (LGFP) was observed in E. coli (FIG. 17). The difference in the growth-suppressing effects in S. cerevisiae and E. coli was thought to depend on the half: .life of mRNA. The half-life of mRNA is a long 22 minutes in yeast, but only a short 2 or 3 minutes in E. coli (Lodish, H. F. et al., (2004), Molecular Cell Biology, W H Freeman & Co., New York). As a result, the concentration within the cell of mRNA of the artificial GFP gene constructed with low usage codons is thought to be maintained at a high level despite the low number of copies of pYLGFP2. The expression level of GFP by pYLGFP2 was much lower than that of pYLGFP1 or pYEG (FIG. 8). Even in eukaryotes, the efficiency of translation is reported to be correlated with the CAI value of the gene (Blake, W. J., Kaern, M., Cantor, C. R. & Collins, J. J., (2003), Nature 422, 633-637; Kellis, M., Birren, B. W. & Lander, E. C., (2004), Nature 428, 617-624). The lgfp (LGFP) gene had a much lower CAI value than yEGFP, but about the same expression level (FIG. 8). The translation efficiency and growth-suppressing effect due to the synthetic GFP gene depended on whether or not numerous types of low usage codons were contained rather than on the CAI value of the gene. The results of this experiment showed that when the expression of a gene containing numerous low usage codons was induced, it was possible that the tRNA was monopolized, resulting in growth suppression not only in prokaryotes but also eukaryotes.

Figure 9:
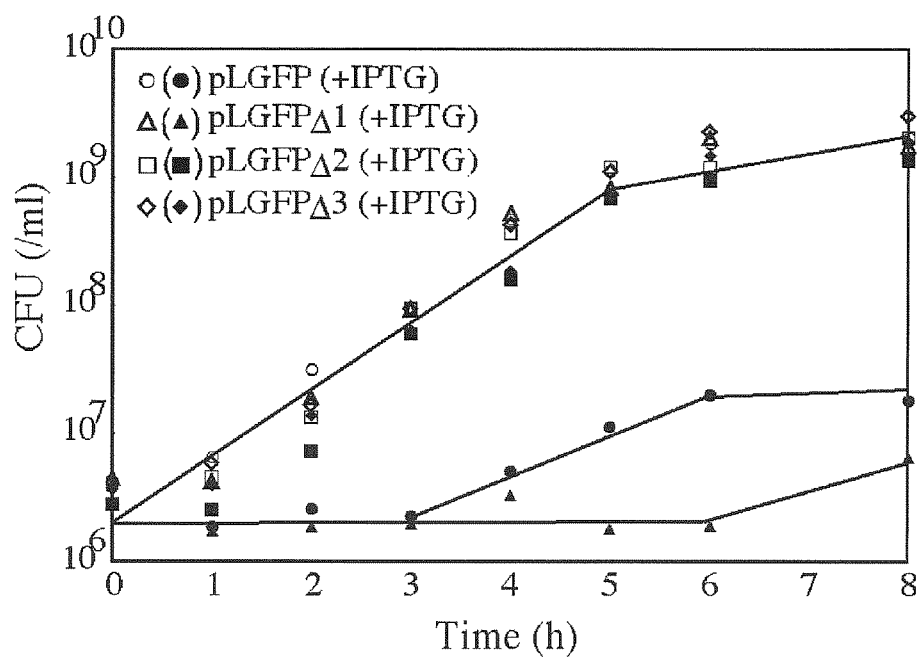
FIG. 9 shows the effect of a mutant lgfp (LGFP) deletion gene on the growth of E. coli. The various symbols indicate the CFU of E. coli containing pLGFP (circles), pLGFPΔ1 (triangles), pLGFPΔ2 (squares), and pLGFPΔ3 (diamonds) when cultured at 37° C. The CFU of E. coli from a culture solution to which a final concentration of 10 mM IPTG was added is indicated by a solid symbol, and the CFU of E. coli from a culture solution to which no IPTG was added by a hollow white symbol.

The Effect of the Length of an Artificial Gene on Suppressing the Expression of a Gene The length of the lgfp (LGFP) gene that was required to suppress the growth of E. coli was examined. Three deletion mutation genes lgfp (LGFP) Δ1, lgfp (LGFP) Δ2, and lgfp (LGFP) Δ3 were prepared in which 25%, 50%, and 75%, respectively, of lgfp (LGFP) was deleted from the C-terminus. In the lgfp (LGFP) gene and in the deletion mutation genes lgfp (LGFP) Δ1, lgfp (LGFP) Δ2, and lgfp (LGFP) Δ3, 111, 83, 59, and 36 rear codons (fraction 0.15), respectively, were present. lgfp (LGFP) Δ1, lgfp (LGFP) Δ2, and lgfp (LGFP) Δ3 were disposed at the lgfp (LGFP) position of plasmid pLGFP to construct plasmids lgfp (LGFP) Δ1, lgfp (LGFP) Δ2, and lgfp (LGFP) Δ3. Even with expression of the deletion lgfp (LGFP) mutant gene, the product did not have fluorescence. When expression of the mutant gene containing lgfp (LGFP) was induced, lgfp (LGFP) and lgfp (LGFP) Δ1 suppressed the growth of E. coli. However, lgfp (LGFP) Δ2 and lgfp (LGFP) Δ3 exhibited no effect whatsoever (FIG. 9). A length of about 500 bp from the N-terminus of the lgfp (LGFP) gene, in which low usage codons were concentrated, was necessary to exhibit a growth-suppressing effect. The number of codons in the form of the rear codon AUA of isoleucine, the lysine codon AAG, and the asparagine codon AAU was reduced in pLGFPΔ1 and pLGFPΔ2 (Table 2). The asparagine codon AAU was not a rear codon. Accordingly, it was not thought to contribute much to the growth-suppressing effect on E. coli. However, the rear codon AUA of isoleucine is not transcribed from the genome, but is synthesized by enzymatic reaction from the methionine codon AUG (Soma, A. et al, (2003), Mol. Cell 12, 689-698).

Figure 10:
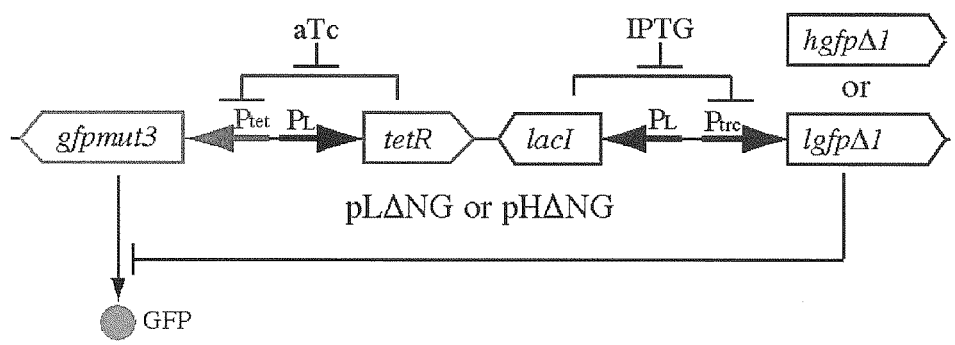
FIG. 10 shows a schematic of the suppression of gene expression by pLΔNG or PHΔNG (control).
Figure 11:
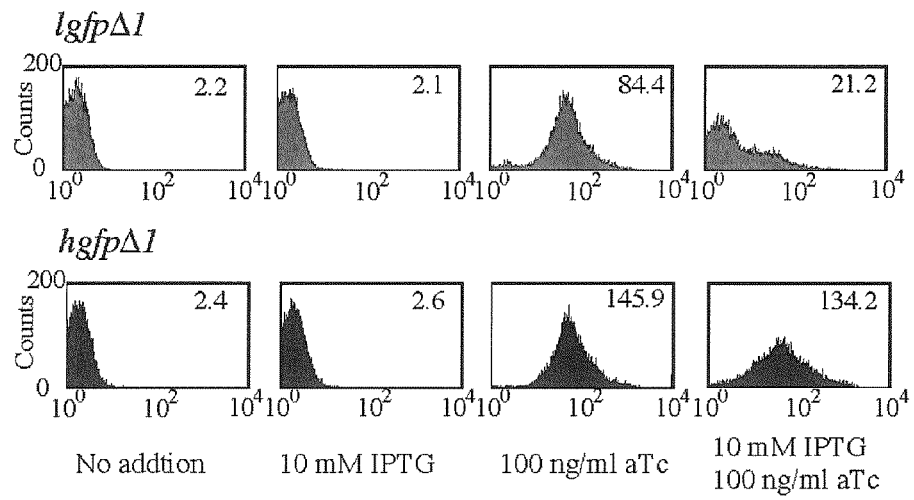
FIG. 11 shows the results of the expression of GFP by pLΔNG and PHΔNG. The numbers in the figure indicate the average values of the GFP expression level.

Suppression of the expression of other genes by artificial gene expression In suppression of the expression of ALP by the expression of the lgfp (LGFP) gene, complete suppression of expression of the gene was not exhibited in E. coli (FIG. 4). It is possible that a number of unknown gene networks and internal cell states control the expression of the pho regulon. Accordingly, to confirm suppression of the expression of the gene after transcription (FIG. 10), plΔNG plasmid was constructed. gfpmut3 gene that contains various use frequency codons and is readily detectable was selected as a reporter gene. The gfpmut3 and lgfp (LGFP) Δ genes were positioned downstream from Ptet (induced by anhydrotetracycline (aTc)) and Ptrc (induced by IPTG), respectively, to permit their expression independently of each other. As a control, a plasmid pH.L1NG was constructed in which lgfp (LGFP) Δ was replaced with hgfpΔ (with the same length from the N-terminus as lgfp (LGFP) Δ). The expression of GFP by the gfpmut3 of plΔNG was about 84.4 when cultured for four hours following the addition of a final concentration of 100 ng/ml of aTc. When expression of lgfp (LGFP) Δ of plΔNG was induced, the level of expression of GFP was found to be suppressed to 21.2, along with the growth of E. coli (FIG. 11). In FIG. 11, the expression of GFP was induced by adding aTc to the medium. The expression of lgfp (LGFP) Δ and hgfpΔ was induced by adding IPTG to the medium to a final concentration of 10 mM. There was no fluorescence in the product of deletion mutation gene lgfp (LGFP) Δ or hgfpΔ.

When expression of hgfpΔ was induced, there was no effect on the growth of E. coli, and GFP expression was maintained at 93.3% of that of the control. This demonstrated that this artificial gene suppressed the expression of another gene. The suppression of the expression of GFP by lgfp (LGFP). t11 was about one-fourth, an effect that was not as great as the suppression of ALP expression (FIG. 4). In this experiment, the gfpmut3 was on a plasmid with multiple copies, and was expressed by a strong Ptet promoter. As a result, a large amount of the mRNA of the gfpmut3 gene was transcribed from pL.t1NG, and the opportunities for binding to various tRNA within the cell were thought to increase.

Suppressing Phage Growth with an Artificial Gene

Figure 12:
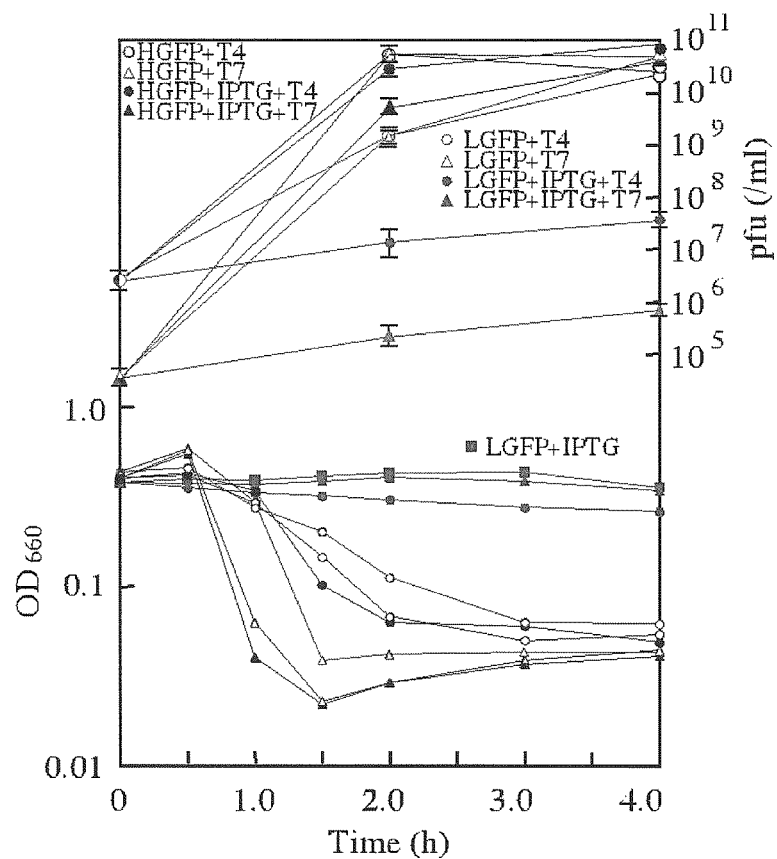
FIG. 12 shows the effect of lgfp (LGFP) expression for T4 or T7 phage infection.

The mechanism of suppressing the expression of a gene with an artificial gene provides new methods of controlling biological activity. One such method is the construction of a non-specific virus defense mechanism. All viruses exploit the translation stage in the expression of host genes for their growth. Thus, the effect on the present gene is thought to be considerable. The effect of the expression of lgfp (LGFP) on the growth of various phages in *E. coli* was examined. The target viruses that were selected were five classical phages: double-stranded DNA phages T4 and T7; A phage, which lysogenizes; single-stranded DNA phage f1; and single-stranded RNA phage MS2 (Birge, E. A., (2000), Bacterial and Bacteriophage Genetics, Springer-Verlag, New York, ed. 4). In the *E. coli* strains K-12 JM2.300 and AK-4 that were employed as phage hosts, the excess expression of the lgfp (LGFP) gene had a growth-suppressing effect (data not disclosed). The *E. coli* was infected with T4 or T7 phage, and the effect of high expression of lgfp (LGFP) on the growth of the phages and bacteriolysis of the host *E. coli* was examined. Further, the same host *E. coli* was induced to highly express hgfp as a control for the lgfp (LGFP) gene. As a result, when lgfp (LGFP) was highly expressed, the various phages grow twenty-times, but no reduction in turbidity due to bacteriolysis was observed. When high expression of hgfp was induced, it was impossible to prevent phage growth or host bacteriolysis (FIG. 12). The experiment of FIG. 12 was conducted as follows. *E. coli* that contained pHGFP (blue) or pLGFP (red) was cultured at 37° C. for 30 minutes with the addition of a final concentration of 10 mM of IPTG (solid symbols) or without the addition of IPTG (hollow white symbols) to the LB medium. The tubidity levels of the respective media were adjusted to an 00660 of 0.4, after which phage T4 (circles) and T7 (triangles) were added. No phage was added to the control (squares). The ratios (moi) of the T4 and T7 added relative to the host bacteria were 0.088 and 0.0012, respectively. When not infected with phage, the *E. coli* containing pHGFP and the pLGFP were retained, and the culture solution of the *E. coli* to which no IPTG was added to induce the lgfp (LGFP) gene was grown for two hours to a stationary phase (data not disclosed). The pfu (upper graph) and 00660 (lower graph) of the various culture solutions were measured over time.

Figure 13:
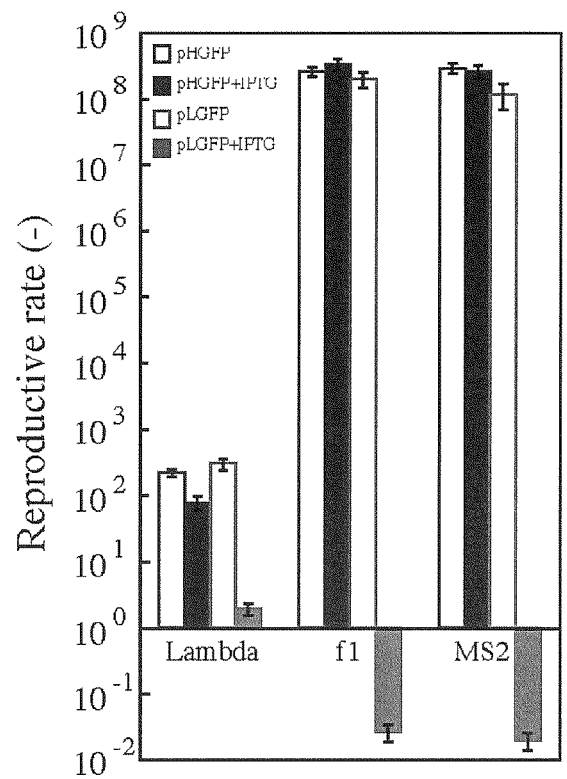
FIG. 13 shows the effect of lgfp (LGFP) expression for various phage growth rates. The bar in the figure gives the standard deviation S.D. (n=3).

Phages T4 and T7 lysed *E. coli* that were expressing hgfp and the turbidity diminished. The phages multiplied to 104 and 106. GFP expression was unaffected by phage infection and growth. Further, when *E. coli* in which the high expression of lgfp (LGFP) gene (FIG. 13) was being induced was employed as a host, lysogenizing A-phage, low toxicity filamentous phage f1, and RNA phage MS2 were unable to grow. Experiment of FIG. 13 was implemented as shown below. *E. coli* JM2.300 carrying pHGFP or pLGFP was employed as host bacterium for A-phage. *E. coli* AK4 carrying pHGFP or pLGFP was employed as host bacterium for phages f1 and MS2. The same culturing conditions and phage infection conditions were employed as in (a). Each of the phages was added to the culture solution to a concentration of moi=0.01. The growth rates of the various phages were calculated from the numbers of plaques formed after four hours of culturing at 37° C.

Figure 15:
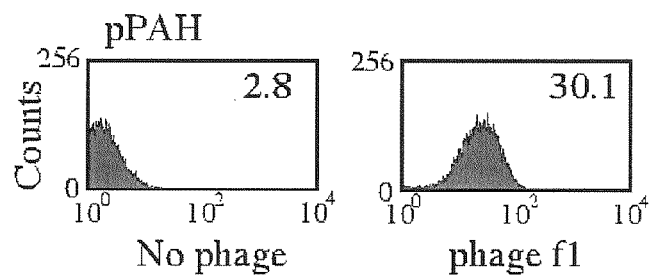
FIG. 15 shows the results of GFP expression by pPAH by phage f1 infection. The numbers in the figure indicate the average values of the GFP expression level.

Phage f1 (moi=1) was added to *E. coli* strain AK-4 carrying pPAH. FIG. 15 shows the results of expression of GFP from pPAH by infection with phage f1 following culturing for two hours at 37° C. FIG. 15 indicates that the GFP expression system was functioning normally.

Figure 16:
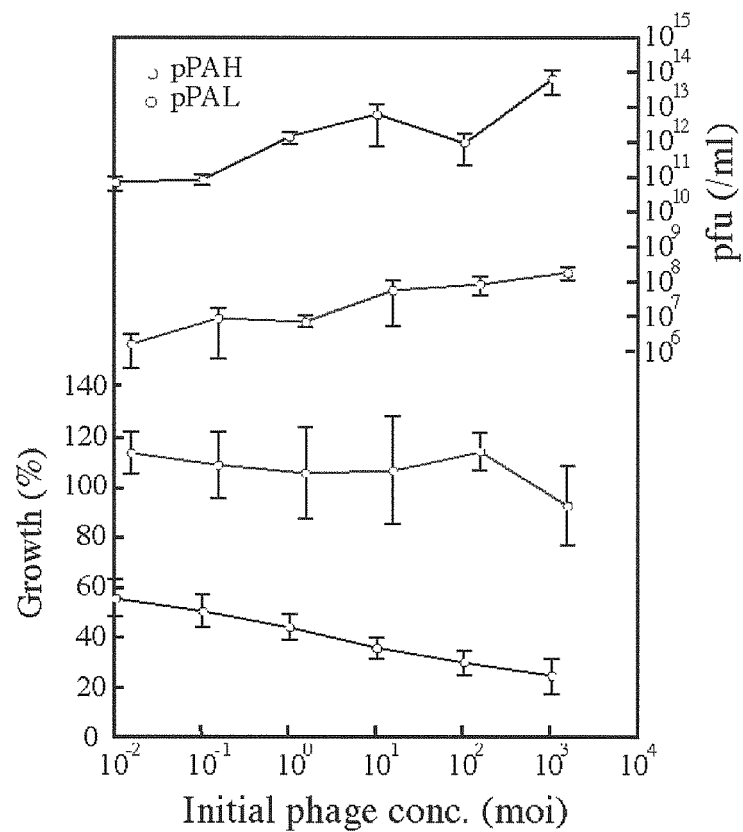
FIG. 16 shows the phage f1 resistance of *E. coli* strain AK-4 containing pPAL. The bar in the figure gives the standard deviation S.D. (n=3).

FIG. 16 shows the phage f1 resistance of *E. coli* strain AK-4 when carrying pPAL. The experiment of FIG. 16 was conducted by adding various concentrations of phage f1 to culture solutions of *E. coli* strain AK-4 holding pPAH (blue) or pPAL (red), and culturing them for four hours at 37° C. A culture solution to which no phage f1 was added was employed as a control. The turbidity ratios of the various culture solutions were calculated and the effect on phage infection was examined (upper graph). The control, which was not infected with phage, grew to a OD660 turbidity of 0.65 to 0.90. The concentration of phage f1 in the culture solutions was measured by the "experimental method" (lower graph).

Four hours after infection, phages f1 and MS2 had particularly decreased to 2% and 3%, respectively, of the initial quantity of phage added. These two phages do not have nuclease (which is present in highly toxic phages to attack host DNA) and thus cannot cut pLGFP within the cell. As a result, the suppression of peptide synthesis by the high expression of lgfp (LGFP) effectively suppressed the synthesis of viral protein and was thought to have suppressed phage growth. These results indicated that *E. coli* cells expressing a high level of lgfp (LGFP) gene could suppress the growth of almost all viruses.

INDUSTRIAL APPLICATION

The methods of the present invention suppress the growth of the cells of various species of living organisms and viruses, permitting use in fields such as biotechnology, bioengineering, and medicine. For example, the methods of the present invention make it possible to suppress tumors and cancer cells; microorganisms such as *E. coli* 0157, which is toxic to the human body, *Salmonella*, and *Legionella*; viruses such as HIV, viral hepatitis, influenza, viral pneumonia, viral bronchitis, and Herpes infections; and the like. Thus, the methods of the present invention permit the treatment of the various diseases caused by these pathogens.

The invention claimed is:

1. A method of suppressing the growth of a target cell, comprising the steps of:
   providing a target cell which is a eukaryotic cell;
   incorporating DNA coding for an arbitrary protein into the target cell; and
   expressing the DNA coding for the arbitrary protein in the target cell into which the DNA has been incorporated,
   wherein the DNA contains nucleotide triplets, each of which is complementary to a codon coding one of the amino acid constituting the arbitrary protein, and having a use frequency of 0.2 or less in the target cell,
   wherein the codon with the use frequency of 0.2 or lower employs tRNA which corresponds to the codon and is necessary for expression of a protein that is essential for the growth of the target cell to suppress the expression of the essential protein, and the suppression of the essential protein suppresses the growth of the target cell.

2. The method according to claim 1, wherein the use frequency is 0.15 or lower.

3. The method according to claim 1, wherein the codon comprised of nucleotide triplets is a single type of codon for a single type of amino acid.

4. The method according to claim 1, wherein the at least a portion of the amino acids is at least three members selected from the group consisting of: alanine, arginine, glycine, isoleucine, leucine, proline, serine, threonine, and valine.

5. The method according to claim 1, wherein the at least a portion of the amino acids is arginine, leucine, and valine.

6. The method according to claim 1, wherein the nucleotide triplets is comprised of at least 80 nucleotide triplets.

7. The method according to claim 1, wherein the DNA is DNA containing regions coding for a promoter and arbitrary protein, the promoter being a promoter of an interferon regulatory factor gene, an interferon gene promoter, an interferon-stimulated response promoter, or a phage shock protein (psp) promoter.

8. The method according to claim 1, wherein the DNA is inserted into a vector and incorporated into the target cell.

9. The method of claim 1, wherein the target cell is a cell of a mammal, bird, reptile, amphibian, fish or plant.

* * * * *